US008119609B2

(12) United States Patent
Lecomte et al.

(10) Patent No.: US 8,119,609 B2
(45) Date of Patent: Feb. 21, 2012

(54) METHODS OF TREATING DIABETIC RETINOPATHY WITH PERICYTE APOPTOSIS INHIBITORS

(75) Inventors: Marc Lecomte, Lissieu (FR); Ulriche Denis, Caluire et Cuire (FR); Clarisse Paget, Lyons (FR); Nicolas Wiernsperger, Orlienas (FR); Michel Lagarde, Decines (FR)

(73) Assignees: Merck Sante (FR); INSERM (FR)

( * ) Notice: Subject to any disclaimer, the term of this patent is extended or adjusted under 35 U.S.C. 154(b) by 0 days.

(21) Appl. No.: 10/421,389

(22) Filed: Apr. 23, 2003

(65) Prior Publication Data

US 2003/0216290 A1 Nov. 20, 2003

Related U.S. Application Data

(63) Continuation of application No. PCT/FR01/03306, filed on Oct. 26, 2001.

(30) Foreign Application Priority Data

Oct. 24, 2000 (FR) ..................................... 00 13640

(51) Int. Cl.
A61K 31/33 (2006.01)
A61K 31/445 (2006.01)
(52) U.S. Cl. ........ 514/44 A; 514/183; 514/315; 514/330
(58) Field of Classification Search .................... 514/12, 514/866, 183, 315, 330, 337, 338, 339, 356, 514/44 A
See application file for complete search history.

(56) References Cited

U.S. PATENT DOCUMENTS

| 5,527,533 | A | | 6/1996 | Tso et al. | |
| 5,585,357 | A | * | 12/1996 | Dolle et al. | 514/18 |
| 6,013,628 | A | * | 1/2000 | Skubitz et al. | 514/12 |
| 6,103,756 | A | | 8/2000 | Gorsek | |
| 6,288,106 | B1 | | 9/2001 | Pearson et al. | |
| 6,800,619 | B2 | * | 10/2004 | Charrier et al. | 514/183 |
| 2002/0086007 | A1 | * | 7/2002 | Sim et al. | 424/94.5 |

FOREIGN PATENT DOCUMENTS

| JP | 09-278652 | | 10/1997 |
| WO | WO 95/17900 | | 7/1995 |
| WO | WO 9623065 A2 | * | 8/1996 |
| WO | WO 96/40647 | * | 12/1996 |
| WO | WO 98/33494 | | 8/1998 |
| WO | WO 98/47534 | | 10/1998 |
| WO | WO 99/02174 | | 1/1999 |
| WO | WO 00/18392 | | 4/2000 |
| WO | WO 00/023421 | * | 4/2000 |
| WO | WO 00/47218 | | 8/2000 |
| WO | 00/59536 | | 10/2000 |
| WO | WO 00/061542 | * | 10/2000 |
| WO | 00/74672 A1 | | 12/2000 |
| WO | WO 01/39792 A3 | * | 6/2001 |
| WO | WO 0139792 A2 | * | 6/2001 |
| WO | 02/34201 A2 | | 5/2002 |

OTHER PUBLICATIONS

Ko, S.C.W., et al., "Functional Characterization of Jurkat T Cells Rescued from CD95/Fas-Induced Apoptosis Through the Inhibition of Capases," Biochemical and Biophysical Research Communications, vol. 270, pp. 1009-1015 (2000).*
Gamen, Susana, et al., "Doxorubin Treatment Activates a Z-VAD-Sensitive Caspase, Which Causes DeltaGammaM Loss, Caspase-9 Activity, and Apoptosis in Jurkat Cells," Experimental Cell Research vol. 258, pp. 223-235 (2000).*
Wang, Jian, et al., "Involvement of Caspase-3 and 8-Like Proteases in Ceramide-Induced Apoptosis of Cardiomyocytes," Journal of Cardiac Failure, vol. 6, No. 3 (2000).*
R&D Systems, Inc. Summary p. For Z-AEVD-FMK, Produced/Updated on Jun. 18, 1999.*
Rudel, T.: "Caspase Inhibitors in Prevention of Apoptosis", Herz 1999:24:236-41, XP-001009833.
Garcia-Calvo et al.: "Inhibition of Human Caspases by Peptide-Based on Macromolecular Inhibitors", Journal of Biological Chemistry, 1998, vol. 273, No. 49, pp. 32608-32613, XP-002222060.
Wei et al.: The Structures of Caspases-1, -3, -7 and -8 Reveal the Basis for Substrate and Inhibitor Selectivity Chemistry and Biology, Current Biology, vol. 7, No. 6, 2000, pp. 423-432, XP001024055.
Kowluru et al.: "Abnormalities of Retinal Metabolism in Diabetes and Experimental Galactosemia", Diabetes, vol. 50, No. 8, Aug. 2001, pp. 1938-1942, XP001064406.
Denis et al.: Advanced Glycation End-Products (AGE) Induce Apoptosis of Cultured Bovine Retinal Pericytes: Implication of Caspases and DAG/Ceramide Production, Diabetes, vol. 50, No. Suppl. 2, Jun. 2001, p. A192, XP-001064430.
Chun et al.: Dopaminergic Cell Death Induced by MPP, Oxidant and Specific Neurotoxicants Shares the Common Molecular Mechanism Journal of Neurochemistry, 2001, 76, pp. 1010-1021, XP002940581.
Schewe, Ionized: Molecular Actkions of Ebselen-An Antiinflammatory Antioxidant, Gen. Pharmac. 1995, vol. 26, No. 6, pp. 1153-1169, XP002940585.
K. Naruse et al.: Aldose Reductase Inhibition Prevents Glucose-Induced Apoptosis in Cultured Bovine Retinal Microvascular Pericytes, Exp. Eye Res., 2000, 71. pp. 309-315, XP-002194076.
Giardino et al.: Aminoguanidine Inhibits Reactive Oxygen Species Formation, Lipid Peroxidation, and Oxidant-Induced Apoptosis, Diabetes, Jul. 1998, vol. 47, pp. 1114-1120, XP-001064401.
Partin, K.: Martindale—The Complete Drug Reference., London: Pharmaceutical Press, 1999, pp. 1052-1054, 1575 and 1636, XP002173135.

(Continued)

Primary Examiner — Kevin E Weddington
(74) Attorney, Agent, or Firm — DLA Piper LLP (US)

(57) ABSTRACT

A method of preventing or treating diabetic retinopathy is disclosed including administering to a mammal a therapeutically effective amount of an inhibitor of retinal pericyte apoptosis. Also disclosed is a pharmaceutical composition which treats and/or prevents diabetic retinopathy comprising as an active agent a therapeutically effective amount of at least one inhibitor of retinal pericyte apoptosis and a pharmaceutically acceptable carrier.

5 Claims, 10 Drawing Sheets

OTHER PUBLICATIONS

Obrosova et al.: Early Changes in Lipid Peroxidation and Antioxidative Defense in Diabetic Rat Retina: Effect of DL-α-Lipoic Acid European Journal of Pharmacology, 398, 2000. pp. 139-146, XP-001011534.

Stefanelli et al.: Nitric Oxide Can Function As Either a Killer Molecule or an Antiapoptotic Effector in Cardiomyocytes, Biochemica et Biophysica 1450, 1999, pp. 406-413, XP-001011533.

Yang et al.: "Intracellular Thiol Depletion Causes Mitochondrial Permeability Transition in Ebselen-Induced Apoptosis", Archives of Biochemistry and Biophysics, Aug. 15, 2000, vol. 380, No. 2, pp. 319-330, XP002940577.

Kowluni et al.: "Abnormalities of Retinal Metabolism in Diabetes or Experimental Galactosemia. VI. Comparison of Retinal and Cerebral Cortex Metabolism, and Effects of Antioxidant Therapy", Free Radical Biology & Medicine, 1999, vol. 26, Nos. 3/4, pp. 371-378, XP-001011532.

Database WPI, "Antioxidizing Agents", Derwent Publications Ltd., 1996 (Abstract) XP002173136.

Avetisov et al.: "Composition for Antioxidant Protection of Eye Media and Tissues—Contains Immobilized Emoxipin and Pyridoxine Hydrochloride", Derwent Publications, Ltd., Dabatase WPI, Dec. 10, 1996, (Abstract) 7 XP00217313.

Ansari at al.: "Prevention of Pericyte Loss by Trolox in Diabetic Rat Retina", Journal of Toxicology and Environmental Health, Part A, 1998, pp. 467-475, XP001011588.

Hammes et al.: Nerve Growth Factor Prevents Both Neuroretinal Programmed Cell Death and Capillary Patholoy in Experimental Diabetes, Molecular Medicine, Jul. 1995, vol. 1, No. 5, pp. 527-534, XP-000908866.

Alnemri, E.S., "Hidden Powers of the Mitochondria," *Nature Cell Biology*, Jun. 1999, vol. 1, pp. 40-42.

Alnemri, E.S. et al., "Human ICE/CED-3 Protease Nomenclature," *Cell*, Oct. 18, 1996, vol. 87, p. 171.

Andrieu, N. et al., "Evidence Against Involvement of the Acid Lysosomal Sphingomyelinase in the Tumor-Necrosis-Factor- and Interleukin-1-Induced Sphingomyelin Cycle and Cell Proliferation in Human Fibroblasts," *Biochem. J.*, 1994, vol. 303, pp. 341-345.

Brett, J. et al., "Survey of the Distribution of a Newly Characterized Receptor for Advanced Glycation End Products in Tissues," *Am. J. Pathol.*, Dec. 1993, vol. 143, No. 6, pp. 1699-1712.

Duan, H. et al., "ICE-LAP3, a Novel Mammalian Homologue of *Caenorhabditis elegans* Cell Death Protein Ced-3 is Activated During Fas-and Tumor-Necrosis-Factor-Induced Apoptosis," *J. Biol. Chem.*, Jan. 19, 1996, vol. 271, No. 3, pp. 1621-1625.

Fernandes-Alnemri, T. et al., "In vitro Activation of CPP32 and Mch3 by Mch4, a Novel Apoptotic Cysteine Protease Containing Two FADD-Like Domains," *Proc. Natl. Acad. Sci. USA*, Jul. 1996, vol. 93, pp. 7464-7469.

Zhu, G. et al., "Stabilization of Proteins Encapsulated in Injectable Poly(lactide-co-glycolide)," *Nature Biotechnol.*, Jan. 2000, vol. 18, pp. 52-57.

Graham, F.I. et al., "Characteristics of a Human Cell Line Transformed by DNA from Human Adenovirus Type 5," *J. Gen. Virol.*, 1977, vol. 36, pp. 59-72.

Hammes, H.P. et al., "Aminoguanidine Treatment Inhibits the Development of Experimental Diabetic Retinopathy," *Proc. Natl. Acad. Sci. USA*, Dec. 1991, vol. 88, pp. 11555-11558.

Hangai, M. et al., "In Vivo Delivery of Phosphorothioate Oligonucleotides into the Murine Retina," *Arch. Ophthalmol.*, Mar. 1998, vol. 116, pp. 342-348, 976-977 (correction).

Lai, C.M. et al., "The Use of Adenovirus-Mediated Gene Transfer to Develop a Rat Model for Photoreceptor Degeneration," *Invest. Ophthalmol. & Vis. Sci.*, Feb. 2000, vol. 41, No. 2, pp. 580-584.

Lander, H.M. et al., "Activation of the Receptor for Advanced Glycation End Products Triggers a $p21^{ras}$-Dependent Mitogen-Activated Protein Kinase Pathway Regulated by Oxidant Stress," *J. Biol. Chem.*, Jul. 11, 1997, vol. 272, No. 28, pp. 17810-17814.

Leeds, J.M. et al., "Pharmacokinetics of an Antisense Oligonucleotide Injected Intravitreally in Monkeys," *Drug Metab. and Dispos.*, 1998, vol. 26, No. 7, pp. 670-675.

Li, W. et al., "Expression of Apoptosis Regulatory Genes by Retinal Pericytes after Rapid Glucose Reduction," *Invest. Ophtamol. & Vis. Sci.*, Aug. 1998, vol. 39, No. 9, pp. 1535-1543.

Lo, T.W.C. et al., "Binding and Modification of Proteins by Methylglyoxal under Physiological Conditions. A Kinetic and Mechanistic Study with Nα-acetylarginine, Nα-acetylcysteine, Nα-acetyllysine, and Bovine Serum Albumin," *J. Biol. Chem.*, Dec. 23, 1994, vol. 269, No. 51, pp. 32299-32305.

Mathias, S. et al., "Signal Transduction of Stress via Ceramide," *Biochem. J.*, 1998, vol. 335, pp. 465-480.

Mizutani, M. et al., "Accelerated Death of Retinal Microvascular Cells in Human and Experimental Diabetic Retinopathy," *J. Clin. Invest.*, Jun. 1996, vol. 97, No. 12, pp. 2883-2890.

Neeper, M. et al., "Cloning and Expression of a Cell Surface Receptor for Advanced Glycosylation End Products of Proteins," *J. Biol. Chem.*, Jul. 25, 1992, vol. 267, No. 21, pp. 14498-15004.

Nunez., G. et al., "Caspases: the Proteases of the Apoptotic Pathway," *Oncogene*, 1998, vol. 17, pp. 3237-3245.

Oganesian, A. et al., "A New Model of Retinal Pigment Epithelium Transplantation with Microspheres," *Arch. Ophthalmol.*, Sep. 1999, vol. 117, pp. 1192-1200.

Podesta, F. et al., "Bax is Increased in the Retina of Diabetic Subjects and is Associated with Pericytes Apoptosis in Vivo and in Vitro," *Am. J. Pathol.*, Mar. 2000, vol. 156, No. 3, pp. 1025-1032.

Preiss, J, et al., "Quantitative Measurement of sn-1, 2-diacylglycerols Present in Platelets, Hepatocytes, and ras-and sis-transformed Normal Rat Kidney Cells," *J. Biol. Chem.*, Jul. 5, 1986, vol. 261, No. 19, pp. 8597-8600.

Schalkwijk, C.G. et al., "Amadori Albumin in Type I Diabetic Patients Correlation with Markers of Endothelial Function, Association with Diabetic Nephropathy, and Localization in Retinal Capillaries," *Diabetes*, Dec. 1999, vol. 48, pp. 2446-2453.

Schmidt, A.M. et al., "Isolation and Characterization of Two Binding Proteins for Advanced Glycosylation End Products from Bovine Lung which are Present on the Endothelial Cell Surface," *J. Biol. Chem.*, Jul. 25, 1992, vol. 267, No. 21, pp. 14987-14997.

Schotte, P. et al., "Non-Specific Effects of Methyl Ketone Peptide Inhibitors of Caspases," *FEBS Letters*, Elsevier Science Publishers, Amsterdam, NL, 1999, vol. 442, pp. 117-121.

Schuchman, E.H. et al., "Human Acid Sphingomyelinase, Isolation, Nucleotide Sequence and Expression of the Full-Length and Alternatively Spliced cDNAs," *J. Biol. Chem.*, May 5, 1991, vol. 266, No. 13, pp. 8531-8539.

Shinohara, M. et al., "Overexpression of Glyoxalase-1 in Bovine Endothelial Cells Inhibits Intracellular Advanced Glycation Endproduct Formation and Prevents Hyperglycemia-Induced Increases in Macromolecular Endocytosis," *J. Clin. Invest.*, Mar. 1998, vol. 101, No. 5, pp. 1142-1147.

Soulis, T. et al., "Advanced Glycation End Products and Their Receptors Co-Localise in Rat Organs Susceptible to Diabetic Microvascular Injury," *Diabetologia*, 1997, vol. 40, pp. 619-628.

Stitt, A.W. et al., "Advanced Glycation End Products (AGEs) Co-localize with AGE Receptors in the Retinal Vasculature of Diabetic and AGE-Infused Rats," *Am. J. Pathol.*, Feb. 1997, vol. 150, No. 2, pp. 523-531.

Su, T. et al., "A Simple Method for the in Vitro Culture of Human Retinal Capillary Endothelial Cells," *Invest. Ophthalmol. & Vis. Sci.*, Sep. 1992, vol. 33, No. 10, pp. 2809-2813.

Thornberry, N.A. et al., "A Combinatorial Approach Defines Specificities of Members of the Caspase Family and Granzyme B," *J. Biol. Chem.*, Jul. 18, 1997, vol. 272, No. 29, pp. 17907-17911.

Wang F. et al., "Inhibition of Sphingolipid Biosynthesis by Fumonisins," *J. Biol. Chem.*, Aug. 5, 1991, vol. 266, No. 22, pp. 14486-14490.

Wilkins, M.R. et al., "Sponge Delivery Variables and Tissues Levels of 5-Fluorouracil," *Br. J. Ophthalmol.*, 2000, vol. 84, pp. 92-97.

Zuckert, W.R. et al., "Modulation of Enzymatic Activity and Biological Function of Listeria Monocytogenes Broad-Range Phospholipase C by Amino Acid Substitutions and by Replacement with the *Bacillus cereus* Ortholog," *Infect. Immun.*, Oct. 1998, vol. 66, No. 10, pp. 4823-4831.

Yan, S.D. et al., "Enhanced Cellular Oxidant Stress by the Interaction of Advanced Glycation End Products with Their Receptors/Binding Proteins," *J. Biol. Chem.*, Apr. 1, 1994, vol. 269, No. 13, pp. 9889-9897.

Yang, Z. et al., "Two Novel Rat Liver Membrane Proteins that Bind Advanced Glycosylation Endproducts : Relationship to Macrophage Receptor for Glucose-Modified Proteins," *J. Exp. Med.*, Sep. 1991, vol. 174, pp. 515-524.

Nuyts, R. M. M. A. et al., "Use of a Polyurethane Patch for Temporary Closure of a Sterile Corneal Perforatian,"*Arch. Ophtalmol.*, Oct. 1999, vol. 117, pp. 1427-1429.

Yamagashi, S. et al., "Receptor-Mediated Toxicity to Pericytes of Advanced Glycosylation End Products: A Possible Mechanism of Pericyte Loss in Diabetic Microangiopathy," *Biochem. and Biophys. Res. Commun.*, Aug. 15, 1995, vol. 213, No. 2, pp. 681-687.

Aiello, L. P. et al, "Diabetic Retinopathy," *Diabetes Care*, Jan. 1998, vol. 21, No. 1, pp. 143-156.

Beisswenger, P. J. et al., "Formation of Immunochemical Advanced Glycosylation End Products Precedes and Correlates with Early Manifestations of Renal and Retinal Disease in Diabetics," *Diabetes*, Jul. 1995, vol. 44, pp. 824-829.

Bierhaus, A. et al., "Advanced Glycation End Product-Induced Activation of NF-?B is Suppressed by$\alpha$-Lipoic Acid in Cultured Endothelial Cells," *Diabetes*, Sep. 1997, vol. 46, pp. 1481-1490.

Cogan, D. G. et al, "Retinal Vascular Patterns," *Archives of Ophthalmology*, Sep. 1961, vol. 66; pp. 100-112.

Degenhardt, T. P. et al., "Chemical Modification of Proteins by Methylglyoxal," *Cellular and Molecular Biology*, 1998, vol. 44, No. 7, pp. 1139-1145.

"The Effect of Intensive Treatment of Diabetes on the Development and Progression of Long-Term Complications in Insulin-Dependent Diabetes Mellitus," *The New Engl. J. of Med.*, The Diabetes Control and Complications Trial Research Group, Sep. 30, 1993, vol. 329, No. 14, pp. 977-986.

"Grading Diabetic Retinopathy from Stereoscopic Color Fundus Photographs—An Extension of the Modified Airlie House Classification," *Ophthalmology*, Early Treatment Diabetic Retinopathy Study Research Group, May 1991, vol. 98, ETDRS Report No. 10, pp. 786-806.

Frank, R. N., "Chapter 1—Diabetic Retinopathy," *Progress in Retinal and Eve Research*, 1995, vol. 14, No. 2, pp. 361-392.

Friedenwald, J. S., "Diabetic Retinopathy. The Fourth Francis I: Proctor Lecture," *American Journal of Ophthalmology*, Aug. 1950, vol. 33, No. 8, pp. 1187-1199.

Jaffrézou, J-P. et al., "Inhibition of Lysosomal Acid Sphingomyelinase by Agents which Reverse Multidrug Resistance," *Biochimica et Biophysica Acta*, 1995, vol. 1266, pp. 1-8.

Kahn, H. A. et al., "Blindness Caused by Diabetic Retinopathy," *American Journal of Ophthalmology*, Jul. 1974, vol. 78, No. 1, pp. 58-67.

Kuwabara, T. et al., "Retinal Vascular Patterns," *Archives of Ophthalmology*, Apr. 1963, vol. 69, pp. 492-502.

Li, W. et al., "Altered mRNA Levels of Antioxidant Enzymes in Pre-Apoptotic Pericytes from Human Diabetic Retinas," *Cellular and Molecular Biology*, 1999, vol. 45, No. 1, pp. 59-66.

Li, W. et al., "Retinal Capillary Pericyte Apoptosis in Early Human Diabetic Retinopathy," *Chinese Medical Journal*, 1997, vol. 110, No. 9, pp. 659-663.

Li, W. et al., "Stimulation of Retinal Capillary Pericyte Protein and Collagen Synthesis in Culture by High-Glucose Concentration," *Diabetes*, Aug. 1984, vol. 33, pp. 785-789.

Mandarino, L. J. et al., "Regulation of Fibronectin and Laminin Synthesis by Retinal Capillary Endothelial Cells and Pericytes in vitro," *Exp. Eye Res.*, 1993, vol. 57, pp. 609-621.

McLellan, A. C. et al., "Glyoxalase System in Clinical Diabetes Mellitus and Correlation with Diabetic Complications," *Clinical Science*, 1994, vol. 87, pp. 21-29.

Nathan, D. M. et al., "Role of Diabetologist in Evaluating Diabetic Retinopathy," *Diabetes Care*, Jan. 1991, vol. 14, No. 1, pp. 26-33.

Palmberg, P. F., "Diabetic Retinopathy," *Diabetes*, Jul. 1977, vol. 26; No. 7, pp. 703-709.

Porta, M. et al., "Growth of Bovine Retinal Pericytes and Endothelial Cells in High Hexose Concentrations," *Diabete & Metabolisme*, 1994; vol. 20, pp. 25-30.

Ruggiero-Lopez, D. et al., "Growth Modulation of Retinal Microvascular Cells by Early and Advanced Glycation Products," *Diabetes Research and Clinical Practice*, 1997, vol. 34, pp. 135-142.

Thornalley, P. J., "Cell Activation by Glycated Proteins. Age Receptors, Receptor Recognition Factors and Functional Classification of AGEs,"*Cellular and Molecular Biology*, 1998, vol. 44, No. 7, pp. 1013-1023.

Thornalley, P. J., "The Clinical Significance of Glycation," *Clin. Lab.*, 1999, vol. 45, pp. 263-273.

"Intensive Blood-Glucose Control with Sulphonylureas or Insulin Compared with Conventional Treatment and Risk of Complications in Patients with Type 2 Diabetes (UKPDS 33)," *The Lancet*, UK Prospective Diabetes Study (UKPDS) Group, Sep. 12, 1998, vol. 352, pp. 837-853.

"Effect of Intensive Blood-Glucose Control with Metformin on Complications in Overweight Patients with Type 2 Diabetes (UKPDS 34)," *The Lancet*, Sep. 12, 1998, UK Prospective Diabetes Study (UKPDS) Group, vol. 352, pp. 854-865.

Bettaíeb, A. et al., "Daunorubiein- and Mitoxantrone-Triggered Phosphatidylcholine Hydrolysis: Implication m Drug-Induced Ceramide Generation and Apoptosis," *Molecular Pharmacology*, 1999, vol. 55, pp. 118-125.

Erkkilä, K. et al., "$N$-Acetyl-$_1$-Cysteine Inhibits Apoptosis in Human Male Germ Cells in Vitro," *Journal of Clinical Endocrinology and Metabolism*, Jan. 1, 1998, vol. 83, No. 7, pp. 2523-2531.

Kolesnick, R. N. et al., "Regulation of Ceramide Production and Apoptosis," *Annual Review of Physiology*, 1998, vol. 60, pp. 643-665.

McClain, D. E. et al., "Trolox Inhibits Apoptosis in Irradiated MOLT-4 Lymphocytes," *FASEB Journal*, Oct. 1995, vol. 9, pp. 1345-1354.

Obrosova, I. G. et al., "Early Changes in Lipid Peroxidation and Antioxidative Defense in Diabetic Rat Retina: Effect of DL-$\alpha$-Lipoic Acid," *European Journal of Pharmacology*, 2000, pp. 139-146.

Singh, I. et al., "Cytokine-Mediated Induction of Ceramide Production is Redox-Sensitive," *The Journal of Biological Chemistry*, Aug. 7, 1998, vol. 273, No. 32, pp. 20354-20362.

Tsao, C-W. et al., "6-Hydroxydopamine Induces Thymocyte Apoptosis in Mice," *Journal of Neuroimmunology*, 1996, vol. 65, pp. 91-95.

Verhaegen, S. et al., Inhibition of Apoptosis by Antioxidants in the Human HL-60 Leukemia Cell Line, *Biochemical Pharmacology*, 1995, vol. 50, No. 7, pp. 1021-1029.

* cited by examiner

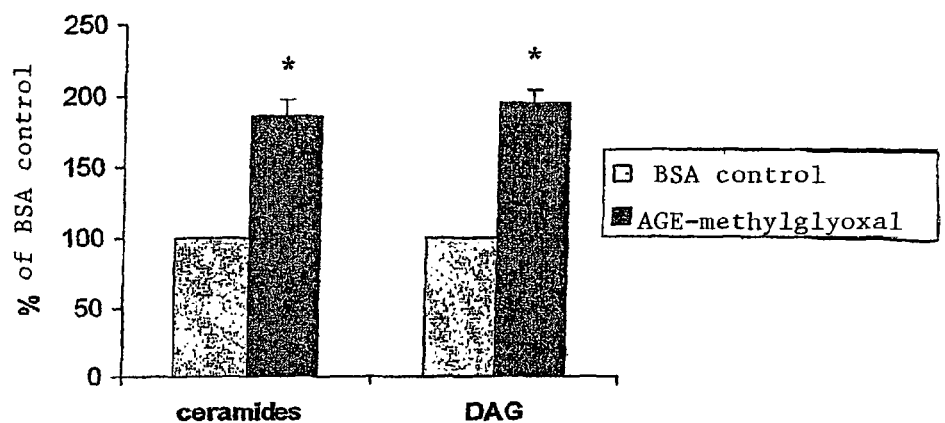
Figure 5
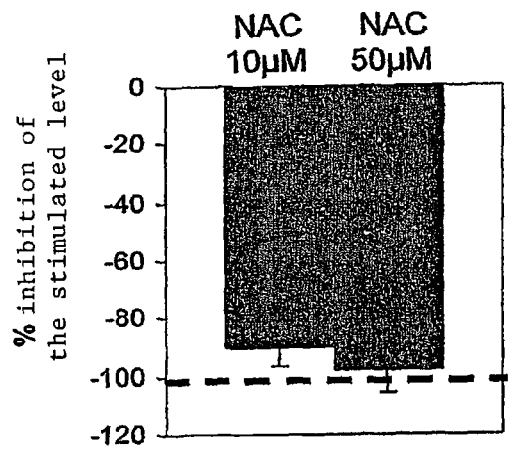
Figure 6    NAC = Nα-acetyl-L-cysteine

NAC = Nα-acetyl-L-cysteine

NAC = Nα-acetyl-L-cysteine

Figure 18    NAC = Nα-acetyl-L-cysteine

METHODS OF TREATING DIABETIC RETINOPATHY WITH PERICYTE APOPTOSIS INHIBITORS

RELATED APPLICATION

This is a continuation of PCT/FR01/03306 filed Oct. 26, 2001, which claims benefit from French Application No. 00/13640 filed Oct. 24, 2000.

FIELD OF THE INVENTION

This invention relates to methods of treating and/or preventing diabetic retinopathy with pericyte apoptosis inhibitors.

BACKGROUND

Diabetic retinopathy represents one of the most debilitating microvascular complications of diabetes. It can lead to blindness in its final stage (Grange, 1995; Frank, 1996; Aiello L P et al., 1998). It is the second leading cause of acquired blindness in developed countries, after macular degeneration of the aged (Nathan et al., 1991). The risk of a diabetic patient becoming blind is estimated to be 25 times greater than that of the general population (Kahn and Hiller, 1974). At present there is no preventive or curative pharmacological treatment for this complication. The only treatment is laser retinal photocoagulation or vitrectomy in the most severe cases (Frank, 1995; Aiello, 1998).

Diabetic retinopathy is a progressive diabetic complication. It advances from a stage referred to as "simple" or initial (background retinopathy) to a final stage referred to as "proliferative retinopathy" in which there is formation of fragile retinal neovessels, leading to severe hemorrhages, sometimes with detachment of the retina, and to loss of vision (Grange, 1995; Frank, 1995). The microvascular lesions in simple retinopathy are characterized by microaneurysms, small petechial hemorrhages, exudates and venous dilations (Palmberg, 1977; ETDRS report no. 10, 1991). This simple retinopathy form can remain clinically silent for a long period of time. At this simple retinopathy stage cellular and structural deterioration of the retinal capillary can be observed in the postmortem examinations of retinas from diabetic patients, compared to the retinas from normal subjects of comparable age. As shown in FIG. 1, the lumens of the retinal capillaries are lined with endothelial cells. Pericytes (or mural cells) are located on the exterior and buried in the basal membrane of the vessel.

In the human retina and the retina of the rat, the numerical ratio of the pericytes to the endothelial cells is one to one (Kuwabara and Cogan, 1963). The alterations observed at this early stage consist of a thickening of the basal membrane of the capillaries (Friedenwald, 1950) and a selective disappearance of the pericytes (Cogan et al., 1961; Kuwabara and Cogan, 1963), diminishing the numerical ratio of the pericytes to the endothelial cells of the retinal capillaries to 0.3 to 1 in the pathological situation and even to 0.1 to 1 for the final stages (Cogan et al., 1961; Kuwabara and Cogan, 1963).

Studies performed on human retinas collected postmortem from patients with diabetes of long duration have shown that the pericytes die from apoptosis, programmed cell death, and not necrosis, the abrupt death seen subsequent to toxic attack (Mizutani et al., 1996; Li et al., 1997; Podesta et al., 2000). But the intracellular signalization pathway(s) by which they disappear is (are) not known.

Detection of apoptotic pericytes was performed in situ on intact retinas by a labeling technique for the nuclei of cells that passed into apoptosis, the TUNEL method (terminal deoxynucleotidyl transferase mediated dUDP nick-end labeling) (Mizutani et al., 1996). Supporting these data, certain pericytes that pass into apoptosis are also stained when use is made of an antibody directed against a protein involved in apoptosis named Bax (Podesta et al., 2000).

Another research team has demonstrated, after purification of the pericytes of retinas from diabetic patients, an augmentation in the expression of the gene of another protein involved in apoptosis, caspase 3 or CPP32 (Cysteine Protease Protein 32 kDa), by detecting an increased mRNA level of this protein by an inverse transcriptase chain polymerization amplification technique (Li et al., 1999). These purified pericytes also show augmented expression of other genes involved in the cellular antioxidant defenses such as that of, e.g., glutathione peroxidase, suggesting that oxidant stress could be involved in the disappearance by apoptosis of the retinal pericytes (Li et al., 1999).

Earlier studies carried out by The Diabetes Control Complications Trial Research Group (DCCT) (1993) and the UK Prospective Diabetes Study Group (UKPDS) (1998 a and b) already demonstrated the key role of the control of hyperglycemia in the development of diabetic retinopathy. Multiple studies determined that glucose, at pathological concentrations, could cause biochemical changes capable of altering the physiological functions or viability of the retinal microvascular cells. The inhibitor effect of glucose in vitro on the proliferation of pericytes, while the growth of endothelial cells is not modified (Porta et al., 1994) could, for example, explain the selective disappearance of pericytes over the course of retinopathy. Similarly, the synthesis of components of the basal membrane (collagen, laminin, fibronectin) stimulated in retinal pericytes and endothelial cells cultured in the presence of glucose (Li et al., 1984; Mandarino et al., 1993) could lead to the thickening of the basal membrane.

Another mechanism by which glucose could lead to vascular complications in diabetes is the increased production and accumulation of advanced products of glycation or AGE (Advanced Glycation End products) formed by the nonenzymic glycosylation or glycation of proteins, DNA or lipids (Maillard reaction, 1912) which have been demonstrated in numerous studies of diabetes (Thornalley, 1999). The amount of AGE measured in the skin of diabetic patients moreover correlates strongly with the severity of the vascular complications (Beisswenger et al., 1995). Glycation or the Maillard pathway shown in FIG. 2 describes the binding of reducing sugars to proteins: a reducing sugar in open form first reacts with the free amine group of basic amino acids contained in the proteins (lysine, arginine), leading to the formation of a Schiff base stabilized subsequently as an Amadori product.

These steps are reversible and dependent on the substrate concentrations (proteins and sugars). After formation of the Amadori product, it undergoes a series of modifications which lead either to an oxidative fragmentation and the formation of products of glycoxidation such as carboxymethyl lysine (CML), or to the formation of dicarbonyls such as 3-deoxyglucosone. These very reactive dicarbonyls in turn react with the protein amines, and thereby propagate the Maillard reaction, forming intramolecular and intermolecular bridges in long-lived proteins (Thornalley, 1999). Other AGE synthesis pathways in addition to glucose have been proposed recently.

Methylglyoxal, formed by the fragmentation of triose phosphates and the oxidation of acetone in the liver (by means of monooxygenases), is another dicarbonyl with an elevated blood concentration in subjects with diabetes (McLellan et al., 1994). In vitro, under physiological pH and temperature conditions, methylglyoxal can irreversibly modify especially the arginine residues of proteins (Lo et al., 1994). Furthermore, the AGE of proteins formed after reaction with methylglyoxal are described as major products observed in diabetes (Degenhardt et al., 1998). The formation of AGE of intracellular proteins after reaction with methylglyoxal, which is more reactive than glucose in the Maillard reaction, appears to be a dominant formation pathway in cells (Nishikawa et al., 2000, Shinohara et al., 1998).

In retinal microvessels, an accumulation of Amadori products, AGE precursors (Schalkwijk et al., 1999), as well as an accumulation of AGE was demonstrated using anti-AGE (or anti-Amadori) antibodies at the level of the basal membrane of pericytes and endothelial cells (Stitt et al., 1997). Multiple studies performed in vitro suggest that AGE could be involved in retinal vascular dysfunction. In fact, AGE modifies the proliferation of both cell types, inhibiting in particular the growth of pericytes (Chibber et al., 1997; Ruggiero-Lopez et al., 1997; Yamagishi et al., 1995). Extracellular AGE is capable of binding to specific membrane receptors and inducing various cellular responses. Studies have shown that there is a co-localization of AGE and AGE receptors in the retinal microvessels of diabetic rats (Stitt et al., 1997; Soulis et al., 1997). These receptors were identified on different cell types, including pericytes (Chibber et al., 1997; Yamagishi et al., 1995; Stitt et al., 1997; Thornalley, 1998) and different types of receptors were isolated: p60, p90 (Yang et al., 1991), RAGE (Receptor for AGE), which is a receptor of the immunoglobulin superfamily (Neeper et al., 1992) complexed to lactoferrin (Schmidt et al., 1992) and galectin 3 (Vlassara et al., 1995). RAGE, the best characterized of the receptors and which is present on the pericytes (Yamagishi et al., 1995; Brett et al., 1993) after having bound an AGE, induced an intracellular oxidant stress (Yan et al., 1994) and activation of the NF-KB transcription factor (Yan et al., 1994) as well as the activation of p21 ras and MAP (Mitogen Activation Protein) kinase (Lander et al., 1997) in the endothelial cells of the umbilical cord vein. Activation of the NF-KB transcription factor in these cells can be inhibited by various antioxidants such as lipoic acid (Bierhaus et al., 1997) and antioxidant enzymes (Yan et al., 1994). The antioxidant trilox can prevent the loss of pericytes in the retina of diabetic rats (Ansari et al., 1998), suggesting that oxidant stress could be involved in the disappearance of pericytes. An antisense RNA directed against the RAGE receptor corrects the AGE antiproliferative effect observed on the pericytes (Yamagishi et al., 1995).

The importance of the Maillard pathway and the accumulation of AGE in the pathogenesis of diabetic complications, and of retinopathy in particular, has been explored notably by using glycation inhibitors such as aminoguanidine, which by its free amine traps the reactive glucose or dicarbonyls, preventing them from reacting with the proteins. In a streptozotocin diabetic rat model, aminoguanidine prevents the accumulation of AGE in the retinal microvessels as well as the disappearance of pericytes and reduces by 80% the number of acellular capillaries in the retina (Hammes et al., 1991).

In contrast, the mechanisms by which AGE brings about the disappearance of pericytes as well as the mode of disappearance—apoptosis or necrosis—of pericytes due to AGE remain questions that are still unresolved.

SUMMARY OF THE INVENTION

This invention relates to a method of preventing or treating diabetic retinopathy including administering to a mammal a therapeutically effective amount of an inhibitor of retinal pericyte apoptosis.

It also relates to a pharmaceutical composition which treats and/or prevents diabetic retinopathy including as an active agent a therapeutically effective amount of at least one inhibitor of retinal pericyte apoptosis and a pharmaceutically acceptable carrier.

The invention further relates to a method of identifying compounds capable of preventing or treating diabetic retinopathy including contacting a pericyte culture treated with AGE with a compound to be tested and evaluating apoptosis of pericytes in the culture to determine capacity of the compound to prevent or treat diabetic retinopathy.

BRIEF DESCRIPTION OF THE DRAWINGS

FIG. 5 shows the effect of AGE-methylglyoxal on the production of ceramides and DAG in bovine retinal pericytes.
FIG. 6 shows the effect of Nα-acetyl-L-cysteine on the apoptosis induced in bovine retinal pericytes by AGE-methylglyoxal.

DETAILED DESCRIPTION

Figure 1:
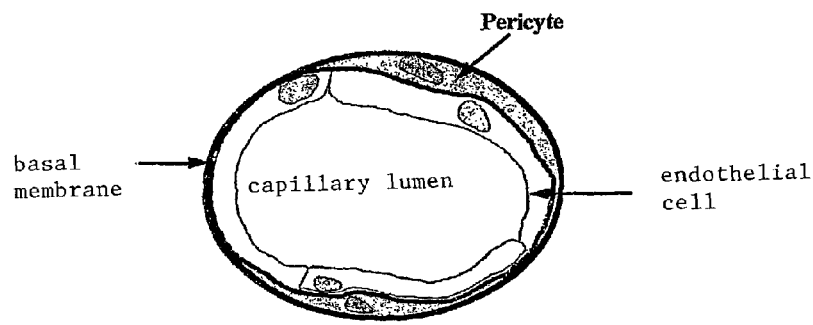
FIG. 1 represents a diagram of a retinal capillary.
Figure 2:
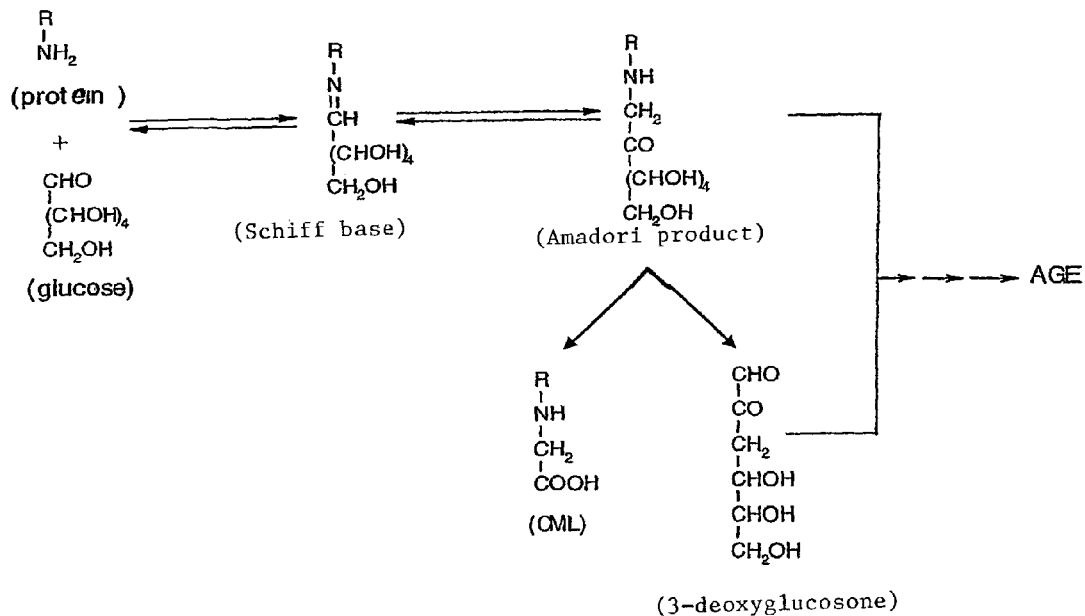
FIG. 2 represents the Maillard pathway.

We have now elucidated the intracellular signalization pathways by which AGE causes the death of pericytes by apoptosis. This enabled us to develop novel methods for preventing or treating diabetic retinopathy comprising administering to a subject a therapeutically effective amount of at least one inhibitor of the apoptosis of the retinal pericytes. The invention is remarkable in that it provides new modes of treating or preventing both clinically established retinopathy and simple retinopathy. The clinical signs of simple retinopathy are generally the appearance of one or two microaneurysms per eyegrounds. The term "diabetic retinopathy" will sometimes be used hereinbelow to refer to established retinopathy as well as simple retinopathy.

Thus, another aspect of the invention is the use of an inhibitor of apoptosis of the retinal pericytes for the preparation of a drug that is useful for preventing or treating diabetic retinopathy.

We have discovered that AGE produced after incubation of albumin with methylglyoxal added to pericyte culture medium (2 μM) over two passages (10-15 days) caused a stimulation of their death by apoptosis (3 times the baseline rate) as well as the intracellular accumulation of ceramides and diacylglycerol (DAG) (200% of the baseline levels). The apoptosis and increased production of ceramides and DAG are normalized in the presence of antioxidants in the culture medium, such as Nα-acetyl-cysteine (NAC) at noncytotoxic concentrations of 10 or 50 μm, suggesting that AGE induces an oxidant stress in the cells and contributes to their death by apoptosis.

Yet another aspect of the invention, therefore, pertains to an antioxidant as an inhibitor of the apoptosis of retinal pericytes. Examples of such antioxidant compounds include Nα-acetyl-L-cysteine, lipoic acid, ebselen, zeaxanthin, coelenteramine, or a derivative or a mixture thereof. The antioxidant compounds are particularly noteworthy because they reduce the production of ceramides and/or DAG. Aspects of the invention, therefore, also envisage compounds capable of directly or indirectly reducing the production of ceramides and/or DAG.

We have also discovered that apoptosis is corrected by antioxidants other than N-acetyl-L-cysteine such as lipoic acid (7 and 14 μM) as well as ebselen (5 and 10 μM), and partially (reduction on the order of 50%) by zeaxanthin (2 μM) as well as coelenteramine (2 μM), all used at noncytotoxic concentrations. Furthermore, we it has now been found that DAG and ceramides are produced by a coupled activation of the specific phospholipase C of phosphatidylcholine (PC-PLC) and acid sphingomyelinase and that the ceramides do not appear to be synthesized de novo.

10,11-dihydro-5-(3-(methylamino)propyl)-5H-dibenz(b,f)azepine, also designated as desipramine (0.1 and 0.3 μM), which is an inhibitor of acid sphingomyelinase, as well as tricyclo(5.21.0(2,6))decyl-(9(8)xanthogenate, also designated D609, (9.4 and 30 μM), which is an inhibitor of PC-PLC, clearly inhibit the production of ceramides but only D609 inhibits both the production of ceramides (95%) and DAG (80%), suggesting that the production of DAG by PC-PLC is located upstream of the activation of the acid sphingomyelinase producing the ceramides. Fumonisin B1 (0.01 μM), inhibitor of the de novo synthesis of ceramides, only marginally inhibits the AGE-induced apoptosis (20%) suggesting that this ceramide production pathway is probably not involved. With regard to apoptosis, it is inhibited by only 50% in the presence of 10,11-dihydro-5(3-(methylamino)propyl)-5H-dibenz(b,f)azepine (desipramine) (0.3 μM) or tricyclo (5.21.0(2,6))decyl-(9(8)xanthogenate (D609) (30 μM) or their combination, whereas the antioxidants protect the cells totally, suggesting a pathway parallel to that of PC-PLC and acid sphingomyelinase causing apoptosis of the pericytes as a result of intracellular oxidant stress.

The invention, therefore, pertains more particularly to the use:

of an inhibitor of phosphatidylcholine-phospholipase C (PC-PLC) as inhibitor of the formation of DAG, and of an inhibitor of acid sphingomyelinase as inhibitor of the formation of ceramides, for the preparation of a drug that is useful for treating and/or preventing diabetic retinopathy. These inhibitors are, in fact, remarkable for their capacity to protect retinal pericytes from apoptosis. Among the inhibitors of phosphatidylcholine-phospholipase C, we can cite more specifically D609 or a derivative thereof. Among the inhibitors of acid sphingomyelinase, we can cite more specifically desipramine or a derivative thereof.

Furthermore, by means of the specific peptide inhibitors of cysteine effector proteases involved in apoptosis, the caspases, we were able to investigate the intervention of caspases in pericyte apoptosis due to AGE. These peptides are chemically modified by a benzyloxycarbonyl group at the N-terminal end (z) and by an (O-methyl)fluoromethyl ketone (fmk) group at the C-terminal end, making them more capable of permeating the cells. The peptides tested with regard to pericyte apoptosis induced by AGE were:

the tripeptide z-VAD-fmk, an inhibitor of all of the caspases;

z-DEVD-fmk, a specific inhibitor of caspase-3, an effector caspase;

z-LEHD-fmk, a specific inhibitor of caspase-9, an effector caspase;

z-LETD-fmk, a specific inhibitor of caspase-8, an initiator caspase;

z-VDVAD-fmk and z-AEVD-fmk, inhibitors respectively of the initiator caspase-2 and caspase-10.

All four peptides z-VAD-fmk (pan caspase inhibitor), z-DEVD-fmk (caspase-3), z-AEVD-fmk (caspase-10) and z-LEHD-fmk (caspase-9) inhibit the apoptosis induced by AGE, but only the peptide z-VAD-fmk inhibited the production of DAG and ceramides, whereas z-DEVD-fmk and z-LEHD-fmk had no effect. This suggests that an initiator caspase is involved upstream of the production of DAG and ceramides and that it is inhibited by z-VAD-fmk. Moreover, two effector caspases, caspase-3 and caspase-9, are involved in the final phase of apoptosis and are inhibited by z-DEVD-fmk and z-LEDH, respectively, and are located after the production of DAG and ceramides, which is not affected by these two peptides.

On the basis of the specificity of the inhibitors employed, the initiator caspase implicated does not appear to be caspase-8 since z-LETD has no effect on apoptosis. In contrast, caspase-10, which is inhibited by z-AEVD-fmk, appears to be implicated since this peptide completely inhibits the pericyte apoptosis induced by AGE. Moreover, z-VDVAD partially inhibits apoptosis, suggesting that the initiator caspase-2 is also implicated. In summary, these studies in particular demonstrated that caspase-2 and caspase-10 could be involved as initiator caspases in the cascade leading to the pericyte apoptosis induced by AGE, and that the effectors caspase-9 and caspase-3 appear to be implicated in the final stage of this apoptosis.

The invention, therefore, pertains to the use of a caspase inhibitor for the preparation of a drug protecting retinal pericytes from apoptosis which is useful for treating and/or preventing retinopathy in a diabetic patient.

Such inhibitors are preferably peptides, advantageously peptides modified chemically by a benzyloxycarbonyl group at the N-terminal end (z) and by an (O-methyl)fluoromethyl ketone group (fmk) at the C-terminal end, increasing their capability to permeate the cells. An example of a peptide caspase inhibitor is the tripeptide z-VAD-fmk, an inhibitor of all of the caspases.

The invention preferably relates the use of an inhibitor of an initiator caspase, preferably selected from among caspase-2 or caspase-10 and/or an inhibitor of an effector caspase, preferable selected from among caspases-3, -6, -7 or -9, most preferably caspase-3 or caspase-9, for the preparation of a drug that is useful for preventing or treating diabetic retinopathy.

An example of an inhibitor of the initiator caspase-10 is the peptide z-AEVD-fmk. An example of an inhibitor of the initiator caspase-2 is the peptide z-VDVAD-fmk. An example of an inhibitor of the effector caspase-9 is the peptide z-LEHD-fmk. An example of an inhibitor of the effector caspase-3 is the peptide z-DEVD-fmk.

The invention also relates to the use of a combination of at least two of the previously cited inhibitors of the apoptosis of retinal pericytes for the preparation of a drug that is useful for treating and/or preventing diabetic retinopathy. Thus, a preferred aspect of the invention includes the conjoint administration to a patient of a therapeutically effective quantity of at least two compounds selected from among:
  an antioxidant compound,
  an inhibitor of phosphatidylcholine-phospholipase C (PC-PLC),
  an inhibitor of an acid sphingomyelinase,
  a caspase inhibitor.

Administration of the inhibitors of the apoptosis of retinal pericytes can be substantially simultaneous or not. The invention, therefore, also includes a pharmaceutical composition comprising as active agent at least one of the previously described inhibitors of the apoptosis of retinal pericytes.

The invention, therefore, relates to a composition comprising as active agent(s) at least one compound selected from among: an antioxidant, a compound that inhibits the production of ceramides and/or DAG, an inhibitor of acid sphingomyelinase, an inhibitor of phosphatidylcholine-phospholipase C, a caspase inhibitor, as previously defined, or a mixture of at least two of these agents. Such a composition is particularly useful for preventing or treating diabetic retinopathy.

Preferred examples of such a composition comprise as active agents, an antioxidant and/or an inhibitor of phosphatidylcholine-phospholipase C (PC-PLC) and/or an inhibitor of acid sphingomyelinase combined in the composition with at least one caspase inhibitor as previously defined.

The composition can be employed in any form of administration known in the art, such as by the oral route (p.o.), by the subcutaneous (s.c.) route, intraperitoneal (i.p.) route or intravenous (i.v.) route, in an adapted formulation whose content of active agent(s) preferably allows a daily administration between about 0.01 and about 200 mg/kg of body weight, preferably between about 0.5 and about 75 mg/kg of body weight, and ideally between about 1 and about 50 mg/kg of body weight, but not limited to these doses, and which can be higher in the case of a compound of low toxicity but of low in vivo activity. For other than ocular administration, the amount of active compound to be combined with the excipient for single dose administration in a composition comprising only a single active component as defined above can vary and depends on the mode of administration. A typical preparation contains from about 5% to about 95% of active compound (w/w). The preparations preferably contain from about 20% to about 80% (w/w) of active compound.

In the case of a composition comprising at least two active compounds as defined above, each of these components is present at a dose ranging from about 10% to about 80% of the dose normally administered in a monotherapy regimen as described above. Upon improvement in the patient's condition, a maintenance dose of a compound, a composition or a combination can be administered if necessary. Similarly, the dose or the frequency of administration can be reduced in relation to the symptoms, and the treatment can be suspended if these symptoms have been limited to the desired level. Similarly, certain patients can require intermittent treatment over the long term until recurrence of one or another symptom of retinopathy.

The formulations for oral administration can be varied: tablets, capsules, powders or solutions containing the active agent(s), as well as pharmaceutically acceptable excipients, taste-masking agents, buffers and preservatives known in the art. The injectable forms contain the active ingredient(s) in a preferably aqueous solvent, possibly with a co-solvent that can reduce the dielectric constant of the medium, containing a salt couple that buffers the pH to values close to physiologic values (pH 7.0-7.4) known in the art and possibly a surface-active agent increasing the solubility of the active ingredient(s).

An especially preferred form of administration consists of topical application or ocular injection. This form of administration can limit the negative general systemic effects that could be caused by prolonged use of orally administered caspase inhibitors. A pharmaceutical composition for an ocular topical application can be formulated in a suitable unguent (ointment, gel or solution) containing the active compound(s) dissolved or in suspension in a vehicle.

Thus, as an example, the composition can be in form of eye drops whose pharmaceutically acceptable vehicles can be isotonic sodium chloride (0.9%, 308 mOsm/l) or isotonic saline solutions comprising sodium chloride, potassium chloride, potassium gluconate, calcium chloride, boric acid, sodium borate or borax, sodium lactate, sodium hydrogen phosphate dihydrate and sodium dihydrogen phosphate dodecahydrate, sorbitol, with or without agents replicating the lachrymal viscosity such as hypromellose 4000 cP, dextran, and preservatives such as sodium edetate, benzododecinium bromide, sodium mercury thiolate, benzalkonium chloride, methyl parahydroxybenzoate, sodium metabisulfite, phenylmercury borate. These compounds are cited as nonlimitative examples of implementation of the invention.

In the case of an ophthalmic ointment or gel, various polymers can be used such as, for example, carbomer 980 NF (polymer of $4 \cdot 10^6$ Da), sorbitol, an oil such as paraffin, sorbitan monostearate, polysorbate 60, cetyl ester wax, cetearyl ester wax, Vaseline, methylcellulose, a fat. Other emulsifiers known in the art can be included in these compositions.

A composition comprises between 0.01 and 10%, preferably between 0.01 and 4%, by weight of the inhibitors to limit risk of undesirable reactions over the long term as well as excessive systemic passage which could lead to suspension of the topical treatment. A typical administration is administration into the conjunctival cul-de-sac, e.g., once or up to four times per day, with a preference for one or two daily administrations.

A drug administration system of the Ocusert (Friederich, 1974) type formed of a reservoir of ellipsoidal shape made of polyacrylate, butylcyanoacrylate or pluronic F127 gel (Desai and Blanchard, 1998) or of fibrin or collagen (Rubin et al., 1973), for example, containing one or more of the previously defined compounds, maintained between two copolymer layers (methylcellulose 15 cP or hydroxypropyl-cellulose 80-120 cP (Desai and Blanchard, 1998)) controlling the administration of the compound(s) over time and placed in the conjunctival cul-de-sac is also an aspect of the invention. A 5×2 mm or 7×4 mm piece of sponge (Altomed™, but also Weck™ and Merocel™) impregnated by the solution containing the active compounds and placed for several minutes in the conjunctival cul-de-sac can also be envisaged for the topical administration of the products (Wilkins et al., 2000).

The compositions can also be formulated in emulsions in which the previously defined compounds are encapsulated in droplets on the order of one micron (liposomes), for example, in soy oil or lecithin, gelatin (Vandervoort and Ludwig, 1999). The viscosity of the preparation can be increased by the addition of methylcellulose or sodium carmellose (Zurowska-Pryczkowska, 1999). The compounds can also be encapsulated in hydroxypropyl-β-cyclodextrins (e.g., a 5% solution) of variable concentration which can be as low as a one-to-one molar ratio in relation to the active ingredient(s) to augment its (their) bioavailability, stability and solubility (Freedman et al., 1993).

The invention also pertains to the use of antisense oligonucleotides complementary of a part of a polynucleotide sequence selected among those coding for a caspase, phosphatidylcholine-phospholipase C or acid sphingomyelinase for preparation of a drug intended for treating and/or preventing diabetic retinopathy.

In fact, the antisense phosphorothioate oligodeoxynucleotides provide the opportunity to modulate the genetic expression of specific genes and have enormous clinical applications. Different antisense oligomers of different sizes, between 6 and 25 nucleotides in length, directed against caspase-2, -3, -9 or -10, or against PC-PLC, or against acid sphingomyelinase, are synthesized and used alone or in combinations.

These antisense oligonucleotides are defined in the caspase sequences close to the N- or C-terminus of these enzymes to avoid cross reactions and to be as specific as possible. The oligonucleotides of PC-PLC are defined either in the C-terminal part or in the N-terminal part, close to the histidines conserved in the active site such as H69 and H118 of the protein of *Listeria monocytogenes* (Zuckert W R et al., 1998).

The oligonucleotides of acid sphingomyelinase are defined in the N-terminal or C-terminal part of the human enzyme (Schuchman et al., 1991) to be as specific as possible and avoid cross reactions. The oligonucleotides are mixed at a concentration between about 1 and about 10 µM in the presence of a polyoxyethylene-polyspermine copolymer or fibrinogen microspheres (Oganesian et al., 1999), on a piece of polytetrafluoroethylene (PTFE) (Karesh, 1987) or polyurethane (Nuyts et al., 1999) membrane. This patch can then be applied inside the eye in the vitreous chamber and in the space located under the retina by a pars plana microsurgical technique (the 2-mm space located 4-5 mm laterally from the corneal-scleral junction) (Algvere et al., 1999) and possibly held in place by means of cement glue containing N-butylcyanoacrylate (Nexacryl™) (Leahey et al., 1993) to allow slow, controlled diffusion over time of these inhibitors.

The antisense oligonucleotides can also be injected as such or encapsulated in liposomes after emulsion with various fats or oils, which are then covered by the viral envelope of the inactivated Japanese hemagglutinating virus (Sendai virus) after fusion, and then injected into the subretinal space via the pars plana (Hangai et al., 1998). The injected doses should advantageously be in the range of about 10 to 200 µg per eye (Leeds et al., 1998) to be active.

The invention also includes implementation of an antisense gene strategy for caspases-2, -3, -9 or -10 in a method for treating and/or preventing diabetic retinopathy. The antisense genes of these caspases are introduced into an adenovirus, as indicated below, which is injected into the subretinal space, after injection via the pars plana as described above (Lai et al., 2000).

The invention also uses cyclic or linear peptides, of two or three amino acids to five or six, competitive inhibitors of caspases, for the preparation of a drug intended for treating and/or preventing diabetic retinopathy.

Such peptides can, for example, be VAD (general caspase inhibitor), DEVD (specific inhibitor of caspase-3), AEVD (specific inhibitor of caspase-10), VDVAD (specific inhibitor of caspase-2) or LEHD (specific inhibitor of caspase-9). These linear peptides are chemically protected at the N-terminal end by an acetyl or benzyl group derivative such as, but not limited to, a benzyloxycarbonyl group (z or BOC), and at the C-terminal end by a methyl ketone group such as but not limited to a fluoromethyl ketone or chloromethyl ketone, or a 2,6-dimethyl group or dichloro benzoylmethyl ketone group, and the lateral chains of aspartic acid amino acids (D) are O-methylated. These peptides can also be coupled to peptides comprised of 16 amino acids and stemming from the hydrophobic sequence of the signal peptide of the Kaposi fibroblast growth factor (FGF), improving their permeability to the cells ($NH_2$-AAVALLPAVLLALLAP-COOH). Derivatives of aspartate alone, protected by a benzyl group and a fluoromethyl ketone group, may also be used. These peptides can be administered by injection, via the s.c., i.p. or i.v. routes, or in topical administration in the conjunctival cul-de-sac, preferably via the i.v. route or topically, and in a formulation enabling a slow, controlled infusion to reduce the frequency of injections in the context of preventive treatment. Such solutions exist and are constituted of preparations of biodegradable polymers containing the peptide and controlling its diffusion such as, but not limited to, an injectable poly(DL-lactid-co-glycolid) (PLGA) in the form (a) either of microspheres having diameters of approximately 1 to 100 µm or (b) a single, cylindrical implant, of a size approximately between 0.8 mm and 1.5 mm in diameter, referred to as a "minicylinder" (Zhu et al., 2000). Stabilization of peptides incorporated in the presence of an antacid such as $Mg(OH)_2$ during encapsulation in the polymer is also possible.

The invention also pertains to the use of a nucleic acid molecule comprising at least one polynucleotide sequence coding for a peptide comprising 2 to 10 amino acids which is a competitive inhibitor of a caspase for the preparation of a drug intended for treating and/or preventing diabetic retinopathy.

The invention also includes a method for treating and/or preventing diabetic retinopathy comprising the above small peptides locally and continuously in situ at the intravitreous and subretinal level. This is advantageously a gene expression strategy of these small peptide caspase inhibitors in the framework of a gene therapy protocol with the vectors currently used for such an approach. For example, the deoxyribonucleotide oligomers corresponding to the peptide sequences of VAD, DEVD, VDVAD or AEVD can by synthesized by automated machines known in the art. In the case of AEVD, it is a matter of producing two complementary oligomers of the following sequences: the coding oligomer 5'-G A T C C (G or A) (T, C, A or G) A T G G C (T, C, A or G) G A (A or G) G T (T, C, A or G) G A (T or C) T A A G-3' and the noncoding oligomer 5'-A A T T C T T A (A or G) T C (T, C, A or G) A C (T or C) T C (T, C, A or G) G C C A T (T, C, A or G) (T, C, A or G) G-3'. After being synthesized, the two oligomers are subsequently phosphorylated by the kinase of the bacteriophage T4, and hybridized to obtain the double-strand DNA sequence corresponding to the AEVD peptide sequence which can then be cloned in the polylinker site containing the sites of suitable restriction enzyme cleavages (BamHI and EcoRI in the case described) of a pAC type expression vector, which can then produce recombinant adenoviruses expressing the desired small peptide by the following strategy.

The pACCMVpLpA vector is produced by inserting the promoter/enhancer of constitutive early genes of cytomegalovirus (CMV), the polylinker (pL) of restriction sites of vector pUC 18, and a fragment of the genome of the simian virus SV 40 which includes the small antigen—T (t) and the polyadenylation signal (pA) in the vector pAC (Gluzman et al., 1982). The double-strand DNA corresponding to the AEVD sequence is then introduced into the vector linearized with the restriction enzymes corresponding to the restriction sites flanking the AEVD sequence, BamH1 and Eco R1 in the example described. The corresponding plasmid is then produced by conventional bacterial cloning techniques, and the insertion is verified by sequencing using the flanking sequence of the polylinker. The resultant plasmid is then co-transfected with pJM17 (McGrory et al., 1988) in 293 cells (human renal embryonic cells transfected by the adenovirus AdEA) (Graham et al., 1977) by co-precipitation of DNA with calcium phosphate. pJM17 codes for an adenovirus 5 of complete genomic sequence interrupted by a bacterial plasmid pBRX at the position 3.7 unity of the genetic map of the adenovirus, thus exceeding the packing limits for the adenovirus.

The homologous recombination between the recombinant plasmid pACCMVpLpA and pJM17 in the 293 cells generates a genome of packable size in which the early region 1 is replaced by the cloned chimeric gene, making the recombinant virus defective for replication. The resultant virus is named AdCMV-AEVD. The presence of the insertion corresponding to the peptide AEVD is confirmed by PCR using the primers flanking the AEVD sequence and sequencing the PCR product obtained. The appropriate viral platelets are then amplified in stocks containing $5$-$50 \times 10^7$ platelet forming units (pfu)/ml and stored in DMEM supplemented with 10% of fetal calf serum. The recombinant adenovirus can then be used and encapsulated by one of the techniques described above and injected via the pars plana into the subretinal space in the intravitreous cavity to have in situ a sustained over time production of caspase inhibitors enabling prevention of the loss of pericytes due to apoptosis.

Finally, the invention pertains to a method for identifying compounds capable of preventing or treating diabetic retinopathy comprising contacting a culture of AGE-treated pericytes with a compound to be tested and evaluating apoptosis in the pericytes to determine the capacity of the compound to prevent or treat diabetic retinopathy. This evaluation advantageously comprises a comparison with apoptosis of a culture of pericytes not treated by the compound and/or not treated by AGE.

The test compound may be selected from among those described above and notably from the group comprising: antioxidants, inhibitors of the production of ceramides and/or of DAG, caspase inhibitors, antisense oligonucleotides of 6 to 25 nucleotides complementary to a part of a polynucleotide sequence selected from among those coding for a caspase, phosphatidylcholine-phospholipase C, acid sphingomyelinase, nucleic acid molecules comprising at least one polynucleotide sequence coding for a peptide of 2 to 10 amino acids which is a competitive inhibitor of a caspase.

Other advantages and characteristics of the invention will become clear from the description below which presents:
1) The effects of AGE-methylglyoxal on bovine retinal pericytes.
2) The induction of an oxidant stress by AGE-methylglyoxal in cultured retinal pericytes.
3) The production pathways of ceramides and DAG activated in retinal pericytes in response to AGE-methylglyoxal.
4) The implication of the caspases.

EXAMPLES

I—Material

1) Reagents

Cell culture products were obtained from Sigma (France) with the exception of FCS (Gibco, France), the collagenase IA and the collagenase/dispase (Boehringer-Mannheim, France). The other reagents were of analytical grade purity and purchased from Sigma (France), with the exception of the silica plates (silica gel 60 G, Merck), the DAG kinase and the ceramides (Tebu, France). The PD-10 columns were obtained from Pharmacia (Sweden). The annexin-V labeling kit was obtained from Boehringer-Mannheim (France). The N-acetyl-L-cysteine, desipramine, lipoic acid and ebselen were obtained from Sigma (France). The caspase-inhibitor peptides were obtained from Calbiochem (France). The fumonisin B1 and the D609 were obtained from Biomol (France).

Preparation of the Solutions of Pharmacological Agents:

The solutions were sterilized with a sterile 0.2 μm Acrodisc filter (Gellman Science).

The mother solution of 1 μM N-acetyl-L-cysteine was prepared as needed: 163.2 mg was added to 1 ml of DMEM and then the solution was filtered in a sterile manner.

A mother solution of coelenteramine at 1.2 mM in ethanol was prepared as needed and added to the cells at a final concentration of 2 μM.

Zeaxanthin was dissolved in sterile DMSO at the concentration of 1.2 mM and added to the cells at a concentration of 2 μM.

A stock solution of 10 mM of ebselen was prepared from 2.74 g of the product added to 1 ml of ethanol. The solution was then divided into aliquot parts and stored at −20° C.

The mother solution of 100 mM of desipramine was prepared as needed: 30.3 mg was added to 1 ml of distilled water. The solution was then filtered in a sterile manner.

A mother solution of 1 mM of fumonisin B1 was prepared from 1 mg added to 1378 μl of distilled water. The solution was then sterilized, divided into aliquot parts, frozen at −180° C. and then stored at −20° C.

The mother solution of 9.4 mM of D609 was prepared as needed: 1 mg of D609 was added to 400 μl of distilled water. The solution was then filtered in a sterile manner.

Stock solutions of 30 mM of the peptides z-VAD-fmk, z-DEVD-fmk, z-AEVD-fmk, z-VDVAD-fmk, z-LETD-fmk and z-LEHD-fmk were prepared from 1 mg of sterile product added respectively to 70, 50, 54, 45, 51 and 42 μl of sterile DMSO. The solutions of all the inhibitors were divided into aliquot parts of adequate volume and then frozen at −20° C.

2) Equipment

The spectrophotometric determinations were performed using the 96-well plate reader iEMS Reader MF (Labsystems). The fluorometer (type LS 50B) was made by Perkin-Elmer. The sonication device (model B 15) was made by Branson. Detection of apoptosis was performed on an Axioplan fluorescence microscope from Carl Zeiss with a Zeiss IV filter, no. 9 (excitation: 450-490 nm; emission >520 nm).

II—Methods
1) Culture of the Bovine Retinal Microvascular Cells (Lecomte et al., 1996)

Freshly enucleated bovine eyes were transported from the slaughterhouse on ice. The extraocular tissue was immediately removed and the eyes were placed in PBS buffer. Subsequent steps were performed in a sterile manner under a laminar flow hood. Two eyes were required for each dish to be cultured. The eyes were briefly plunged into 70% ethanol then rinsed in HBSS medium (without either $Ca^{2+}$ or $Mg^{2+}$). They were dissected 5 mm posterior to the cornea, the anterior chamber of the eye with the crystallin as well as the vitreous contained in the ocular globe were removed. The neuronal retinal was detached from the ocular globe, cut at the level of the optic nerve and placed in HBSS buffer at 4° C. This buffer was prepared from HBSS without either $Mg^{2+}$ or $Ca^{2+}$ containing 10 mM of HEPES at pH 7.4, 100 U/ml of penicillin and 100 µg/ml of streptomycin. After 10 minutes of oxygenation (95% $O_2$; 5% $CO_2$), BSA at 22% was added until reaching a final concentration of 0.5%; the pH was then adjusted to 7.4 with several drops of NaOH (monitoring the curve of the phenol red indicator). The contaminant pigment cells were removed and the retinas, in groups of two, were placed in 10 ml of clean HBSS buffer on ice. The retinas were cut into pieces with scissors (pieces of circa 2 mm), homogenized (Dounce 15 ml, piston A) prior to being centrifuged (300 g, 5 minutes, 4° C.).

Pericyte Cultures (Bovine Retinal Pericytes)

Two bovine retinas were used for each dish (6 cm in diameter) to be cultured. Each batch of two retinas was processed and homogenized as described above in 10 ml of HBSS buffer at 4° C. The homogenate was centrifuged (300 g, 5 minutes, 4° C.) and the residue resuspended in 5 ml of an enzymatic solution of collagenase/dispase. This collagenase/dispase solution (1 mg/ml) prepared in HBSS medium without $Mg^{2+}$ or $Ca^{2+}$ containing 10 mM of HEPES at pH 7.4, 100 U/ml of penicillin and 100 µg/ml of streptomycin, was then oxygenated for 10 minutes and the pH adjusted to 7.4 prior to addition of TLCK (147 ng/ml) and DNase (200 U/ml). The digestion was allowed to continue for 20 minutes at 37° C. and the cell residue resuspended manually at the mid-incubation point. The suspension was then filtered on a sterile nylon filter with a mesh size of 70 µm. The microvessel fragments contained on the filter were recovered in HBSS buffer (the filter was rinsed twice), centrifuged (300 g, 5 min, 4° C.) and washed once in the same buffer. After centrifugation (300 g, 5 minutes, 4° C.), the microvessel fragments were resuspended in 3 ml of DMEM containing 10% FCS, 2 mM of glutamine and the antibiotics. The microvessel fragments were cultured in a Petri dish (6 cm in diameter) coated with 100 µg of fibronectin (4 µg/cm$^2$) in 2 ml of DMEM for 3-4 hours at 37° C. (Su and Gillies, 1992). After having allowed the microvessels to become attached for 3 hours at 37° C., the medium and the debris that had not adhered to the matrix were eliminated and 3 ml of culture medium was added. The medium was constituted by DMEM with 10% fetal calf serum (FCS), 80 mg/ml of heparin, glutamine and the antibiotics. The cells were maintained in an incubator at 37° C. under an atmosphere of humidified air containing 5% $CO_2$. The culture medium was replaced at the end of 24 hours and then every 48 hours until confluence was attained.

Upon attaining confluence, the culture medium was eliminated and the cells trypsinated with 1 ml of a 0.5% solution of trypsin and 0.2% of EDTA until the cells became rounded (about 5 minutes) after examination with the phase-contrast microscope. The trypsin was then inactivated with 2 ml of culture medium containing the serum and the cells recovered and then centrifuged (180 g, 3 minutes, 4° C.). The subcultured cells in a 1:3 ratio were sown in three dishes (6 cm in diameter), recovered with fibronectin and cultured in the same medium.

2) Culture of Pericytes in the Presence of Advanced Glycation Products (AGE)

The effects of AGE were tested on a uniform batch of cells (bovine retinal pericytes stemming from the same primary culture). When they were at confluence, the bovine retinal pericytes in primary culture were trypsinated. After having allowed them to become attached for 4 hours at 37° C., the medium and the cell debris that had not adhered to the matrix were eliminated and the culture medium (10% of FCS for bovine retinal pericytes) was added. An AGE solution (or its control) was added to the culture medium until reaching a concentration of 20 µM to test the effects of AGE. The cultures were then continued for 1 or 2 passages with the agents, either for 7 or 15 days, respectively, for the bovine retinal pericytes.

Preparation of the AGE

"AGE-methylglyoxal" was prepared by incubating 7.2 mg/ml of BSA and 100 mM of methylglyoxal for 50 hours at 37° C. (Westwood and Thornalley, 1995). The BSA control was obtained by incubating albumin under the same conditions, but without methylglyoxal. The glycated proteins were characterized by their fluorescence (370-440 mm), their fixation to cultured endothelial cells, mononuclear phagocytes and purified RAGE (Yan et al., 1994). The different preparations were then desalinated on PD-10 columns (2.5 ml of the preparations were filtered and recovered in 3.5 ml of DMEM).

3) Determination of the Proteins by Staining With Amide Black on Nitrocellulose Membrane The proteins were determined using the method described by Schaffner and Weissmann (1973). The samples containing the proteins to be determined were brought up to 270 µl with PBS prior to the addition of 30 µl of Tris-HCl buffer (1 M, pH 7.5) containing 1% of SDS, then 60 µl of trichloroacetic acid at 60%. These solutions were vortexed, allowed to stand for 2 minutes at ambient temperature for precipitation of the proteins and each was then filtered at the level of a previously noted reference point on a 0.45 µm nitrocellulose filter wet with 6% TCA. A standard range with 0 to 27 µg of BSA was prepared in parallel. Filters were then immersed for several minutes in an amide black solution at 0.1% (w/v, in methanol: acetic acid:water, 45:10:45, v/v/v). The filters were then rinsed in a water bath and then in the decoloration solution (methanol: acetic acid:water, 90:2:8, v/v/v) until the membrane became completely white except at the level of the protein deposits. The filter was dried, the deposits cut out and the stain fixed on the proteins was eluted with 1 ml of elution solution (ethanol:water:NaOH: EDTA, 100:100:0.1:1.9, v/v/w/w) (circa 10 minutes, vortexing regularly). The reading was performed on 300 µl of these solutions (96-well plate) at 620 nm; quantification was performed using the Biolise software program.

4) Immunocytochemical Evaluation of Apoptosis in Pericytes Cultured in the Presence of AGE Apoptosis was detected and quantified in pericytes cultured during two passages with 2 µM of AGE-methylglyoxal or its control using the technique based on detecting apoptotic cells with annexin V and detecting necrotic cells with propidium iodine.

Staining With Annexin V:

The presence of phosphatidylserine (PS) on the external layer of the plasma membrane, which is characteristic of apoptotic cells, can be detected using annexin V labeled with fluorescein. This protein has a very strong affinity for PS. Staining is performed in the presence of an intercalating DNA dye, propidium iodine, similar to ethidium bromide to distinguish the apoptotic cells from possibly present necrotic cells which also fix annexin V. For this labeling the pericytes must be subconfluent (75% of confluence) and, thus, cultured for only about 12 days with AGE-methylglyoxal or BSA control.

The bovine retinal pericytes (dish 3.5 cm in diameter) were rinsed three times with PBS then incubated for 10 minutes in the dark with 500 μl of a HEPES buffer containing 10 μl of the fluorescein-labeled annexin V solution and 10 μl of the propidium iodine solution provided in the determination kit. The apoptotic cells as well as the necrotic cells fixed the annexin V and thus appeared green under the fluorescence microscope, but only the nuclei of the necrotic cells were dyed red by the propidium iodine. The percentages of necrotic cells and apoptotic cells were determined on 10 different fields, i.e., on a total of 300 to 800 cells.

5) Determination of the Ceramides and Diacylglycerols (DAG)

Figure 3:
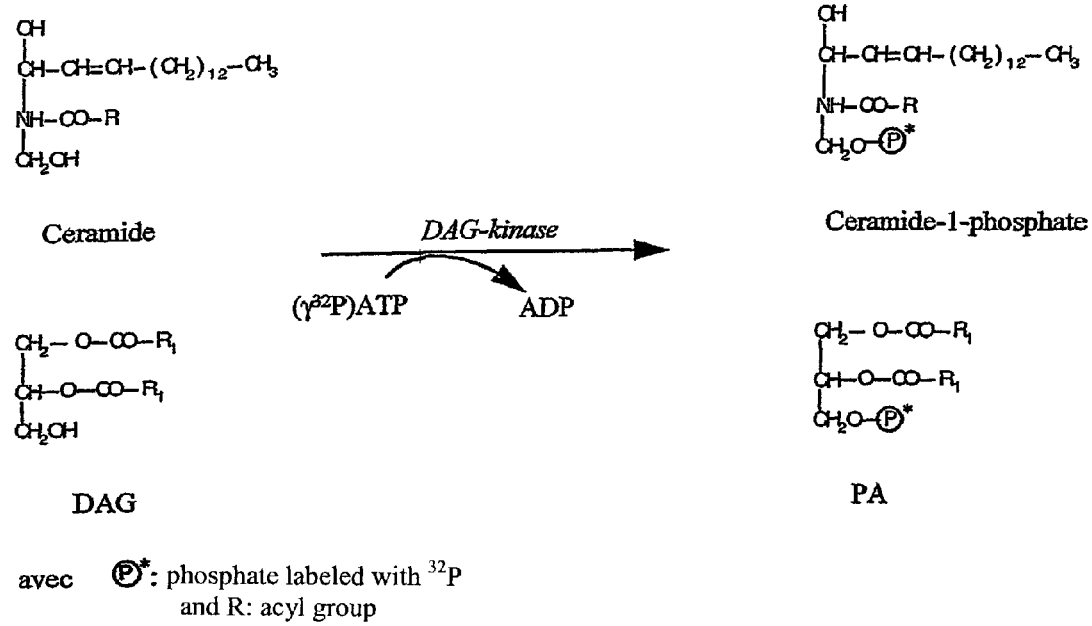
FIG. 3 represents the $^{32}P$ labeling of ceramides and DAG.

The ceramides and diacylglycerols were measured in the pericytes cultured during two passages with 21M of AGE-methylglyoxal or their control according to the method described by Preiss et al. (1986). This method is based on the phosphorylation of the ceramides and DAG by purified diacylglycerol kinase (DAG-kinase) from Escherichia coli in the presence of ATP labeled with $^{32}P$ on the γ phosphor in accordance with the diagram shown in FIG. 3.

The pericytes (2 or 3 dishes, 6 cm in diameter) were rinsed, recovered by scraping with a rubber policeman in 0.5 ml of water on ice and the dish rinsed by a supplementary 0.5 ml (volume of 1 ml of cell suspension) to which was added 10 μl of a solution of (9,10-$^{3}H$)-triacylglycerol at 0.5 μCi/ml.

5.1) Extraction of the Total Lipids

The total lipids were then extracted by the method of Bligh and Dyer (1959). To this cell suspension (1 ml of PBS) was added 3.75 ml of a chloroform: methanol (2:1, v/v) mixture containing 80 μl of BHT (5 mM) in solution in ethanol. The solutions were then vortexed for 30 seconds and allowed to stand for a minimum of 30 minutes, then 1.25 ml of NaCl (0.9%) and 1.25 ml of chloroform were added to separate the phases. After centrifugation (700 g, 5 minutes), the bottom organic phase was collected and extraction of the aqueous phase was repeated twice with 1.5 ml of chloroform. The lipid extracts were then collected and the chloroform evaporated under a nitrogen stream. The aqueous phase enabled determination of the total proteins by staining with amide black and the organic phase was recovered in an Eppendorf tube then evaporated under nitrogen.

5.2 Phosphorylation With DAG Kinase

A standard range of ceramides (25 to 2500 ng) and DAG (25 to 25,000 ng) containing the same quantity of tritium-labeled triacylglycerol was prepared in parallel. The lipids were then solubilized in 20 μl of a solution of detergents (7.5% of n-octylglucopyranoside, mM of cardiolipin and 1 mM of DETAPAC) by 1 minute of sonication followed by incubation for 15 minutes at ambient temperature. The reaction was started by addition of 50 μl of reaction buffer (imidazole 100 mM, NaCl 100 mM, MgCl$_2$ 25 mM, EGTA 2 mM, pH 6.6), 20 μl of a solution of DAG-kinase (4.86 mU) containing 10 mM of DTT and 10 μl of [γ-$^{32}P$] ATP at 5 mCi/ml diluted 10-fold in a solution containing 10 mM of unlabeled ATP, 100 mM of imidazole and 1 mM of DETAPAC (pH 6.6). The reaction was allowed to continue for 1 hour at ambient temperature and then stopped by 1 ml of the mixture chloroform:methanol: 1N hydrochloric acid (100:100:1, v/v/v), 170 μl of a buffer containing 10 mM of HEPES, 135 mM of NaCl, 1.5 mM of CaCl$_2$, 0.5 mM of MgCl$_2$ and 5.6 mM of glucose (pH 7.4) then 30 μl of EDTA 100 mM. The mixture was then vortexed, allowed to stand for 15 minutes at ambient temperature, then centrifuged (10,000 g, 5 minutes) at ambient temperature.

The organic phase (bottom) was collected and evaporated under nitrogen. The lipids were then taken up with 300 μl of the mixture ether:methanol (9:1, v/v) and deposited on a silica plate. The ceramides-1-phosphate were separated from the phosphatidic acid and triacylglycerols using the mixture chloroform:methanol: acetic acid (65:15:5, v/v/v) as migration solvent.

Exposure of the silica plate to an autoradiographic film (30 minutes, 80° C.) allowed visualization of the different $^{32}P$-labeled lipids. The spots corresponding to the ceramides-1-phosphate and phosphatidic acid as well as the last 3 cm before the migration front (corresponding to the triacylglycerols) were delimited with a graphite crayon and scratched. The silica was recovered in counting pots, moistened with 200 μl of methanol, 200 μl of distilled water and 2 ml of scintillation liquid (Picofluor) for 2 hours before the addition of 8 ml of the scintillation liquid. The radioactivity emitted by the $^{32}P$ or the $^{3}H$ was then counted in each pot. The radioactivity emitted by the mother solution of (9,10-$^{3}H$)-triacylglycerol was also counted which allowed calculation of the reaction yield for each sample. The quantities of ceramides and diacylglycerols present in each sample were then determined after extrapolation from the standard range, taking into account the yield, and presented as the quantity of total proteins.

Part B: Results

I—Effects of Age-Methylglyoxal on the Bovine Retinal Pericytes

The toxic effect of AGE-glucose on the proliferation of retinal pericytes was demonstrated in earlier in vitro studies (Ruggiero-Lopez et al., 1997).

The study focused most particularly on the effects of AGE-methylglyoxal on the retinal pericytes. Methylglyoxal appears to manifest its greatest effect in diabetes. Methylglyoxal is a dicarbonyl whose blood concentration is greatly increased in diabetic subjects (McLellan et al., 1994). Moreover, the advanced products of glycation derived from methylglyoxal were described as the major chemical modifications observed over the course of chronic diseases such as diabetes (Degenhardt et al., 1998).

The bovine retinal pericytes were cultured during two passages (approximately 15 days) in the presence of AGE-methylglyoxal to mimic the chronicity of a diabetic environment, since the initial objective of the study was testing to determine whether AGE-methylglyoxal induces pericyte apoptosis and whether this phenomenon is associated with an increased production of ceramides and DAG.

1) Pericyte Apoptosis in Response to AGE-Methylglyoxal

Figure 4:
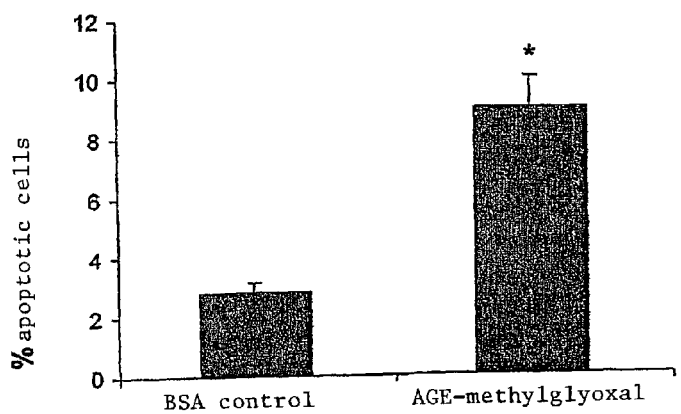
FIG. 4 shows the effect of AGE-methylglyoxal on apoptosis of bovine retinal pericytes.

Apoptosis was detected and quantified by labeling with annexin V and propidium iodine in bovine retinal pericytes during two passages with 2 μM of AGE-methylglyoxal or their control (see Material and Methods). This technique revealed translocation of phosphatidylserine from the internal layer to the external layer of the plasma membrane, a biochemical phenomenon characteristic of the early phase of apoptosis. Fluorescein-labeled annexin V stained green the plasma membranes of the apoptotic and necrotic cells, but only the necrotic cells whose cells had lost their integrity, were permeable to propidium iodide which stained their nuclei red. FIG. 4 shows the effect of AGE-methylglyoxal on the apoptosis of bovine retinal pericytes. The cells were cultured during two passages (approximately 15 days) in the presence of 2 μM of AGE-methylglyoxal or control BSA. The results are expressed as % of apoptotic cells in the total cell population.

The proportion of apoptotic cells represented 8.9±1.1% (mean±SEM, n=10, p<0.05) of the total of the pericytes cultured with 2 μM of AGE-methylglyoxal versus only 2.9±0.34 of the cells cultured with 2 μM of control BSA. Thus AGE-methylglyoxal induced an augmentation by a factor of about 3 on average in the pericyte apoptosis rate. No necrotic cells were observed.

2) Production of Ceramides and DAG in the Pericytes

To determine whether the ceramides and DAG could be implicated in the transduction signal leading to apoptosis, these two compounds were determined in pericytes incubated during two passages (circa 15 days) with 2 μM of AGE-methylglyoxal or their control. The determination technique employed was based on the phosphorylation of the ceramides and DAG by DAG-kinase in the presence of radioactive ATP ($^{32}P$) (see Material and Methods). FIG. 5 shows the effect of AGE-methylglyoxal on the production of ceramides and DAG in bovine retinal pericytes. The results are expressed as % variation from the control cells cultured with control BSA.

A stimulation of the production of ceramides (+85±12%) (mean±SEM, n=10, p<0.05) and of DAG (+94±9%) was demonstrated in the bovine retinal pericytes in response to AGE-methylglyoxal.

3) Conclusion

Labeling with annexin V and propidium iodide of cells cultured during 15 days with 2 μM of AGE-methylglyoxal allowed detection of an augmentation in the apoptosis rate of bovine retinal pericytes by a factor on average of 3. This suggests that AGE-methylglyoxal induces over the long-term apoptosis of pericytes in culture. The disappearance of retinal pericytes due to apoptosis has been described in vitro in response to abrupt glucose fluctuations (Li et al., 1996) and ex vivo in the retina of diabetic patients and rats (Mizutani et al., 1996; Li et al., 1997). The alteration of the expression of apoptosis regulatory genes (mRNA of the protein Bax) has also been demonstrated in pericytes cultured over the long term with high concentrations of glucose then subjected to a rapid reduction in glucose (Li et al., 1998) and in the pericytes of retinas recovered postmortem from diabetic patients (Podesta et al., 2000).

In contrast, the induction of apoptosis of the retinal pericytes by AGE (AGE-glucose and AGE-methylglyoxal) has never been previously demonstrated. Pericyte apoptosis induced by AGE-methylglyoxal is associated with a stimulation of the production of ceramides and DAG, thereby demonstrating that these two compounds are implicated in the transduction of the apoptotic signal. The research presented below consisted of describing the signalization pathway leading to pericyte apoptosis in response to AGE-methylglyoxal.

II—Induction of an Oxidant Stress by Age-Methylglyoxal in Cultured Retinal Pericytes Earlier studies revealed an erosion of the antioxidant capacities of bovine retinal pericytes in response to AGE-glucose (20 μM). An augmentation of the activities of catalase and Cu/Zn SOD as well as a reduced quantity of thiols were observed in pericytes cultured on a chronic basis with AGE-glucose, suggesting a compensatory response of the cells faced with increased production of free radicals and thus an oxidant stress (Paget et al., 1998). A decrease in the markers of lipid peroxidation, TBARS and isoprostanes were also observed as a mirror reflection of a stimulation of the antioxidant defenses (Paget et al., 1998).

We investigated the implication of an antioxidant stress in the signalization pathway leading to apoptosis by studying the effects of different classes of antioxidants on the induced apoptosis of pericytes and on the stimulated production of ceramides and DAG in response to AGE-methylglyoxal.

1) The Different antioxidants Tested

The antioxidants tested can be classified into three groups on the basis of their molecular structure and mode of action. The first group comprises the water-soluble compounds possessing a thiol function which has the capacity to furnish a proton: this group includes Nα-acetyl-L-cysteine (NAC) and lipoic acid. These two agents have a protector effect of the redox balance of the cell cytoplasm. The second type of antioxidant tested is ebselen, a synthetic molecule containing a selenium atom. This compound has the particularity of mimicking selenium-dependent glutathione-peroxidase activity (Se-GPx). It thereby induces a protection of the membranes against lipid peroxidation. The third group is constituted of liposoluble compounds rich in conjugated double bonds which have a high reactivity in relation to free radicals and thereby protect more specifically the membranes against lipid peroxidation. This group includes zeaxanthin and coelenteramine.

2) Effects of N-acetyl-L-cysteine

FIG. 6 shows the effect of Nα-acetyl-L-cysteine on the apoptosis (annexin V, see Material and Methods) induced in bovine retinal pericytes by AGE-methylglyoxal. The pericytes were cultured during two passages (from 12 to 15 days) in the presence of 2 μM AGE-methylglyoxal (or the BSA control) and 10 μM or 50 μM of N-acetyl-L-cysteine. The results, expressed in % inhibition of the apoptosis induced, are the means of 5 independent experiments.

At the two concentrations tested, N-acetyl-L-cysteine protected the pericytes against the apoptosis induced by AGE-methylglyoxal.

Figure 7:
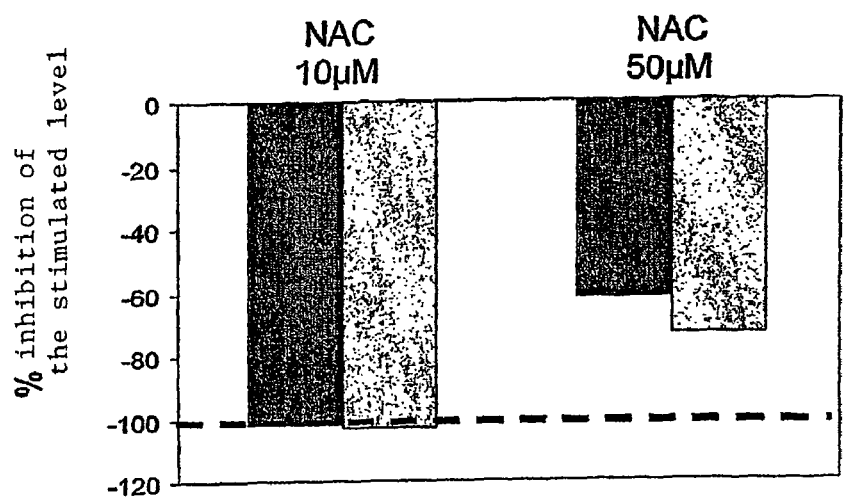
FIG. 7 shows the effect of Nα-acetyl-L-cysteine on the production of ceramides and DAG in bovine retinal pericytes induced by AGE-methylglyoxal.

The ceramides and DAG were also determined in the bovine retinal pericytes cultured in the presence of N-acetyl-L-cysteine (see FIG. 7). The ceramides and DAG were determined in the manner described in the Material and Methods section. The results, expressed as % of inhibition of stimulated production of ceramides and DAG, are the means of 2 independent experiments. The addition of 10 μM of N-acetyl-L-cysteine to the culture medium totally inhibits the production of ceramides and DAG induced by AGE-methylglyoxal (−100%). In contrast, treatment of the cells with 50 μM of N-acetyl-L-cysteine only induces a partial inhibition of this overproduction (−60% of the overproduction of ceramides and −70% of the overproduction of DAG). This partial effect can probably be explained on the basis of a pro-oxidant effect of an antioxidant employed at an excessively high concentration.

The complete inhibition of the induced apoptosis of the pericytes cultured in the presence of 10 μM of N-acetyl-L-cysteine was associated with a parallel total inhibition of the overproduction of ceramides and DAG. This suggests that AGE-methylglyoxal induces an oxidant stress located upstream of the production of ceramides and DAG as well as the apoptosis of the pericytes.

Figure 8:
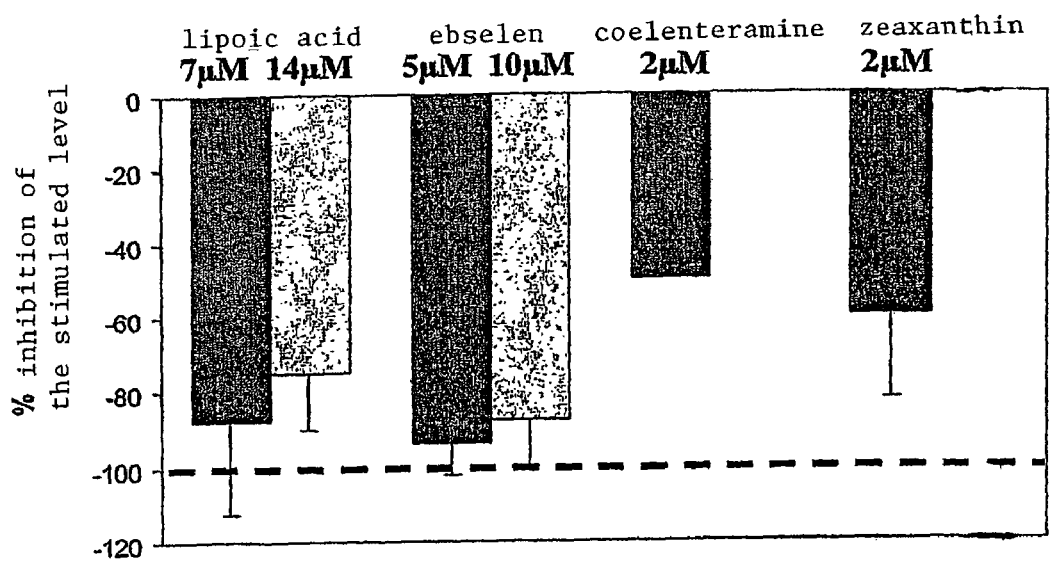
FIG. 8 shows the effect of various antioxidants on pericyte apoptosis in response to AGE-methylglyoxal.

3) Effects of Various Antioxidants on Pericyte Apoptosis in Response to AGE-Methylglyoxal The protective effect of Nα-acetyl-L-cysteine on the disappearance of pericytes in response to AGE-methylglyoxal was confirmed by testing different antioxidants. FIG. 8 shows the effects of the antioxidants on pericyte apoptosis in response to AGE-methylglyoxal. The results, expressed in % inhibition of the induced apoptosis, are the means of 3 independent experiments except for coelenteramine (2 independent experiments).

The addition to the culture medium of lipoic acid at the concentrations of 7 µM and 14 µM inhibited, respectively, by 88% and 75% the pericyte apoptosis (annexin V, see Material and Methods) induced by AGE. Incubation of the cells with 5 µM and 10 µM of ebselen blocked, respectively, by 94% and 88% the apoptosis induced by AGE-methylglyoxal. In contrast, treatment of the pericytes with 2 µM of coelenteramine and 2 µM of zeaxanthin only created a partial inhibition of the induced apoptosis by 60% and 50%, respectively. This moderate effect of the two liposoluble antioxidants can perhaps be explained by the fact that these two agents were not tested at higher concentrations: a vehicle effect (DMSO) was seen on the apoptosis of pericytes in response to AGE-methylglyoxal.

Incubation of the pericytes with different antioxidants enabled protection of the cells from apoptosis. This result clearly confirms the induction of an oxidant stress in the signalization pathway of the pericyte apoptosis induced by AGE-methylglyoxal.

III—Pathways for the Production of Ceramides and DAG Activated in Retinal Pericytes in Response to AGE-Methylglyoxal Our work was also directed to defining the pathways for the production of ceramides and DAG activated in the pericytes cultured with AGE-methylglyoxal. We determined that the different possible pathways for the production of ceramides. On the one hand, ceramides can stem from the de novo biosynthesis pathway. Two metabolic intermediaries, sphingosine and sphinganine, are acetylated by a sphinganine-acyl-transferase to form ceramides. The ceramides can also be the production of enzymatic hydrolysis: they can stem on the one hand from part of the pool of sphingomyelins and, on the other hand, from the pool of glycosphingolipids (ceramides linked to one or more glycannic chains) (Mathias et al., 1998; Okasaki et al., 1998).

Similarly, the DAG production pathways are of two types. They can originate from an activation of the de novo biosynthesis pathway or stem from enzymatic hydrolyses: the DAG can be liberated from a pool of phosphatidylinositol biphosphates or from a pool of phosphatidyl cholines under the action of specific phospholipases.

We investigated the production pathways of these two metabolic intermediaries using a pharmacological approach. The cells were cultured in the presence of different enzymatic inhibitors, the effects of which were analyzed in terms, on the one hand, of induced apoptosis and, on the other hand, with regard to the stimulated production of ceramides and DAG in response to AGE-methylglyoxal.

1) The Production Pathway of Activated Ceramides in the Pericytes a) Implication of a sphinganine-acyl-transferase To investigate whether the de novo biosynthesis pathway is activated in response to AGE-methylglyoxal, the effect of fuminisin B1 (Wang et al., 1991), a specific inhibitor of sphinganine-acyl-transferase, on pericyte apoptosis was tested.

Figure 9:
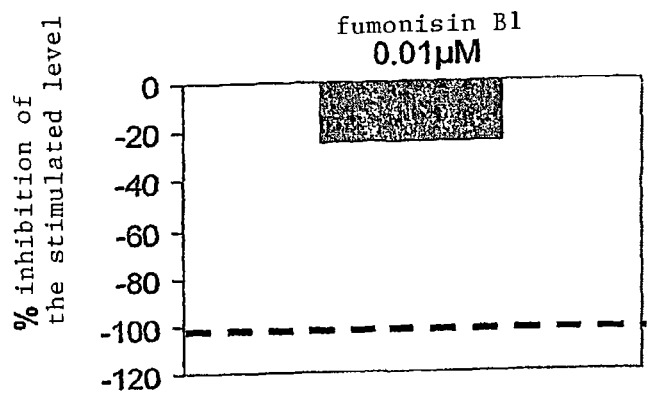
FIG. 9 shows the effect of fumonisin B1 on pericyte apoptosis induced by AGE-methylglyoxal.

FIG. 9 shows the effect of fuminisin B1 on pericyte apoptosis induced by AGE-methylglyoxal. The results, expressed in % inhibition of the induced apoptosis, are the means of 2 independent experiments. The addition of 0.01 µM of fumonisin B1 to the culture medium only induced an inhibition of 22% of the apoptosis of pericytes (annexin V, see Material and Method) cultured during two passages (circa 15 days) in the presence of AGE-methylglyoxal (or BSA control). Fumonisin B1 at 0.1 µM was also tested. At this concentration, fumonisin B1 was proapoptotic because it only affected the base apoptosis rate of cells cultured in BSA control (results not shown).

Fumonisin B1 did not protect pericytes from induced apoptosis. Thus de novo synthesis does not appear to be implicated in the retinal pericyte apoptosis induced by AGE-methylglyoxal.

b) Implication of an Acid Sphingomyelinase

Ceramides can be formed from the pool of sphingomyelins under the action of sphingomyelinases. The various sphingomyelinases are distinguished by their intracellular localization and their optimal activity pH: thus, there are acid, neutral and basic sphingomyelinases.

The implication of an acid sphingomyelinase was investigated by analyzing the effects of a specific inhibitor of this enzyme, desipramine (10,11-dihydro-5(3-(methylamino)propyl))-5H-dibenz(b,f)azepine) (Andrieu et al., 1994; Jaffrezou et al., 1995) on the induced apoptosis of the cells and the stimulated production of ceramides and DAG in pericytes cultured with AGE-methylglyoxal.

Figure 10:
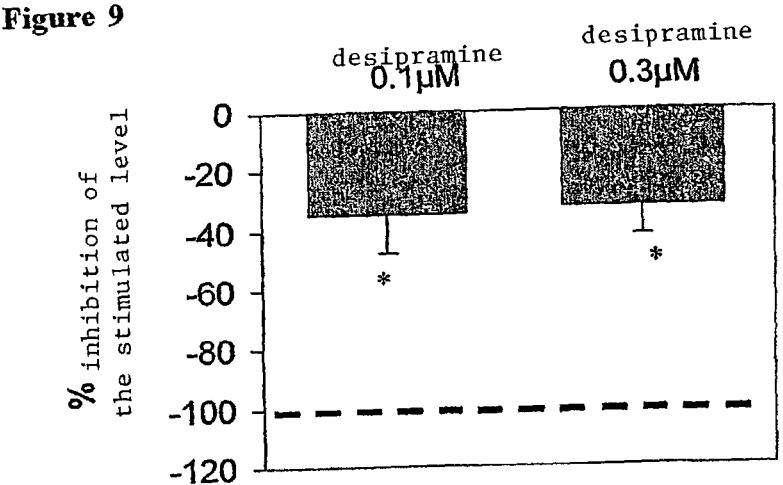
FIG. 10 shows the effect of desipramine on pericyte apoptosis induced by AGE-methylglyoxal.

FIG. 10 shows the effect of desipramine on pericyte apoptosis induced by AGE-methylglyoxal. The results, expressed in % inhibition of the induced apoptosis, are the means of 7 independent experiments for desipramine at 0.1 µM and of 6 independent experiments for desipramine at 0.3 µM. A pericyte culture during two passages (circa 15 days) in the presence of AGE-methylglyoxal with 0.1 µM and 0.3 mM of desipramine exhibited a partial inhibition of 35% of the apoptosis induced by AGE-methylglyoxal (FIG. 10). Desipramine at 1 µM was also added to the culture medium but under these conditions, the baseline apoptosis rate of the control cells was affected (results not shown).

Figure 11:
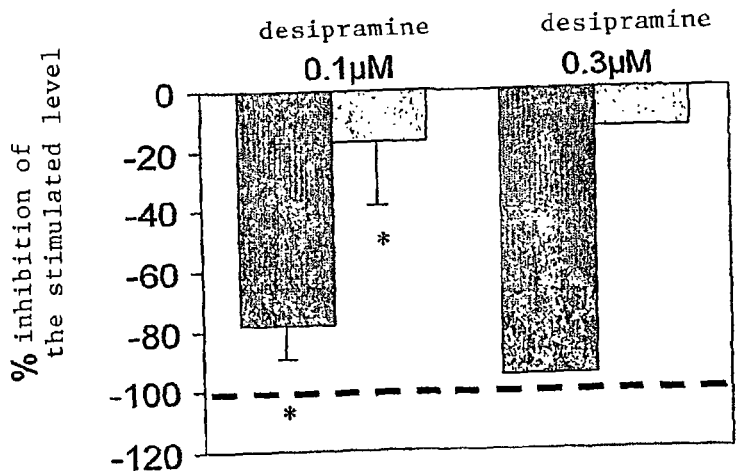
FIG. 11 shows the effect of desipramine on the stimulated production of ceramides and DAG in bovine retinal pericytes induced by AGE-methylglyoxal.

FIG. 11 shows the effect of desipramine on the stimulated production of ceramides and DAG in bovine retinal pericytes induced by AGE-methylglyoxal. The ceramides and DAG were determined as described above. The results, expressed in % inhibition of stimulated production of ceramides and DAG, are the means of 4 independent experiments for desipramine at 0.1 µM and 2 independent experiments for desipramine at 0.3 mM. Desipramine at 0.1 µM added to the culture medium during two passages blocked 78% of the ceramides produced in the pericytes in response to AGE-methylglyoxal but only reduced the overproduction of DAG by 17%. The inhibitor effect of desipramine at 0.3 µM on the stimulated production of ceramides appeared to be dose dependent because the tested agent induced an inhibition of 95% of the ceramides formed. The overproduction of DAG was only blocked by 13%. The addition of 1 µM of desipramine to the culture medium affected the baseline levels of the ceramides and DAG in the cells cultured with BSA control (results not shown).

c) Conclusions

Treatment of the pericytes with 0.3 µM of desipramine induced a complete inhibition of the ceramides produced without affecting the overproduction of DAG: the augmentation of the ceramides observed in the pericytes cultured with 2 mM of AGE-methylglyoxal is clearly linked to the activation of an acid sphingomyelinase. This enzyme could be coupled to a specific phospholipase C of the phosphatidylcholines (PC-PLC) (Schütz et al., 1992; Genestier et al., 1998). Thus, in the pericytes cultured with 2 µM of AGE-methylglyoxal, the action of a PC-PLC on a pool of phosphatidylcholines would release DAG which would activate in cascade an acid sphingomyelinase inducing the formation of ceramides. When the cells are cultured with desipramine, the acid sphingomyelinase is inhibited: this results in a drop in the production of ceramides whereas there is no affect on DAG which is produced upstream of the enzymatic target.

Figure 12:
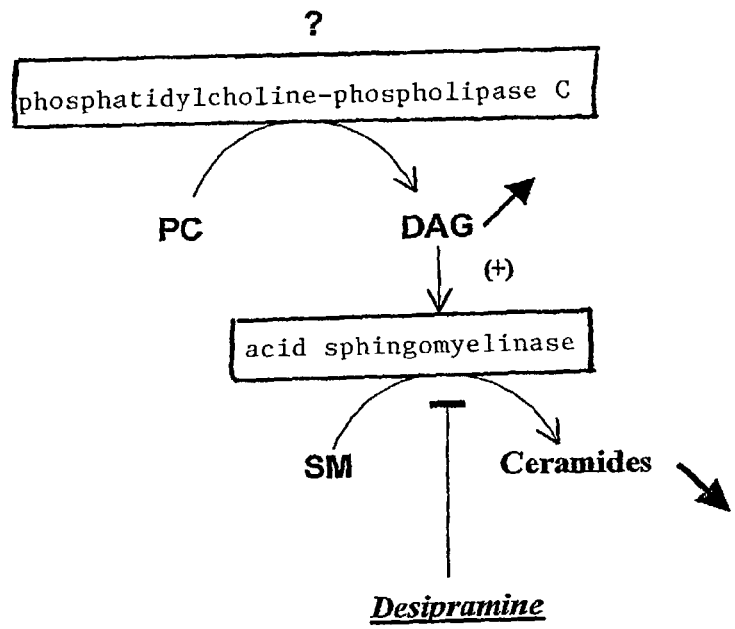
FIG. 12 represents the production pathway of ceramides and DAG in pericytes envisaged on the basis of the invention.

FIG. 12 presents the production pathway of the ceramides and DAG in the pericytes envisaged on the basis of the invention. Although the overproduction of ceramides was totally blocked, desipramine only partially protects the pericytes against the apoptosis induced by AGE-methylglyoxal.

2) Production Pathway of the DAG Activated in the Pericytes a) Implication of a Phosphatidylcholine-Phospholipase C To confirm the hypothesis proposed for the production pathway of the ceramides and DAG and to investigate whether the DAG are implicated in the residual apoptosis, the effects of a specific inhibitor of phosphatidylcholine-phospholipase C, D609 (tricyclo(5.21.0(2.6))decyl-9(8)xanthogenate) (Müller-Decker et al., 1988; Müller-Decker, 1989) on the induced apoptosis (FIG. 13) and on the production of ceramides and DAG induced by AGE-methylglyoxal (FIG. 14) were analyzed.

Figure 13:
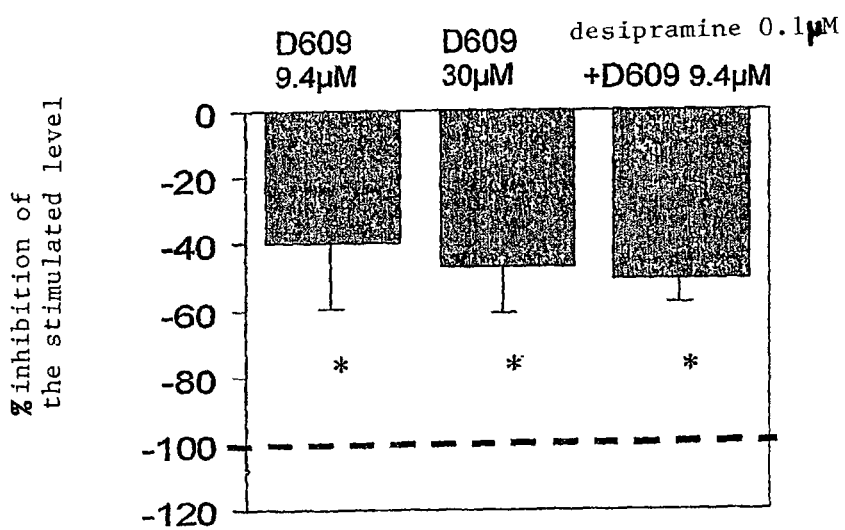
FIG. 13 shows the effect of D609 on pericyte apoptosis induced by AGE-methylglyoxal after two passages.

FIG. 13 shows the effect of D609 on the apoptosis (annexin V, Material and Methods) of the pericytes induced by AGE-methylglyoxal after two passages. The results, expressed as % inhibition of the induced apoptosis, are the means of 7 independent experiments for D609 at 9.4 µM and of 6 independent experiments for D609 at 30 µM and the combination desipramine/D609. The addition of 9.4 µM and 30 µM of D609 to the culture medium allowed blocking, respectively, 40% and 47% of the pericyte apoptosis induced by AGE-methylglyoxal. We also tested the combination 0.1 µM of desipramine with 9.4 µM of D609 with the goal of acting simultaneously on both enzymatic targets. Treatment of the cells by the two combined agents induced an effect equivalent to that of D609 by itself: the pericyte apoptosis was inhibited by 51%.

Figure 14:
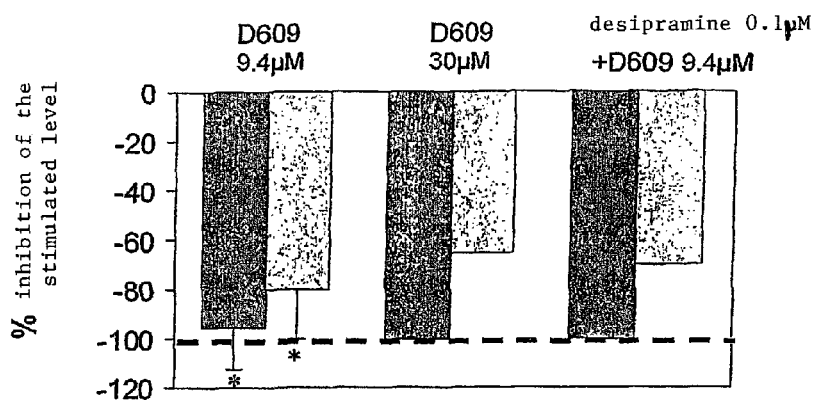
FIG. 14 shows the effect of D609 on the stimulated production of ceramides and DAG in bovine retinal pericytes induced by AGE-methylglyoxal.

FIG. 14 shows the effect of D609 on the stimulated production of ceramides and DAG (see Material and Methods) in bovine retinal pericytes induced by AGE-methylglyoxal. The results, expressed as % inhibition of the stimulated production of ceramides and DAG, are the means of 4 independent experiments for D609 at 9.4 µM and 2 independent experiments for D609 at 30 µM and the combination desipramine/D609. Incubation of the cells in the presence of 9.4 µM of D609 induced an almost total inhibition of the production of the ceramides DAG of 95% and 80% of the stimulated levels, respectively. At the concentration of 30 µM, D609 caused a complete inhibition of the production of ceramides and an inhibition of 65% of the DAG produced. Treatment of the cells by the two agents combined induced an effect equivalent to that of D609 at 30 µM: the overproduction of ceramides was totally blocked and 70% of the DAG produced under the effect of AGE-methylglyoxal was inhibited.

b) Conclusion

Incubation of the pericytes with D609, more particularly at the concentration of 9.4 µM, induced a parallel inhibition of the stimulated production of ceramides and DAG. This result thus allows us to conclude that the formation of DAG is clearly linked to the activation of a phosphatidylcholine-phospholipase C coupled to an acid sphingomyelinase, which validated the previously envisaged production pathway for the ceramides and DAG.

Nevertheless, despite a complete inhibition of the ceramides and DAG, the cells are only partially protected against the apoptosis induced by AGE-methylglyoxal, which suggests the existence of a second signalization pathway parallel to the production of ceramides and DAG and leading to apoptosis of the pericytes.

Figure 15:
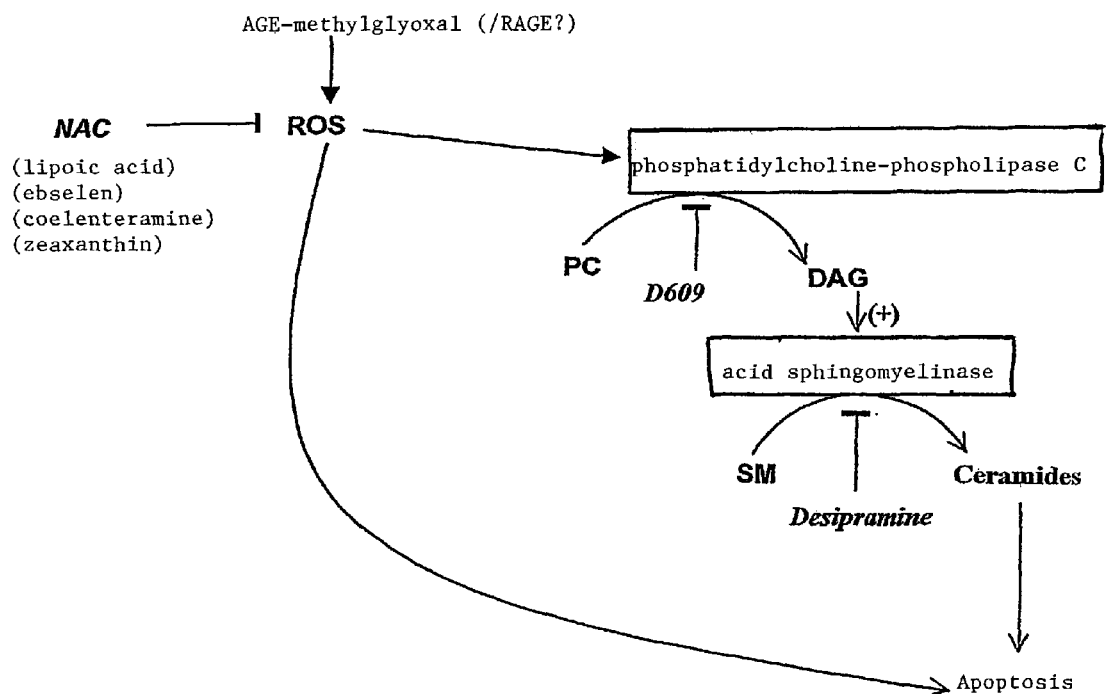
FIG. 15 represents the signalization pathway leading to pericyte apoptosis envisaged on the basis of the invention.

FIG. 15 shows the signalization pathway leading to apoptosis of the pericytes.

AGE-methylglyoxal, probably by the intermediary of a specific AGE receptor, induces an oxidant stress which can be located at the intersection of two signal transduction pathways leading to apoptosis of the pericytes. In fact, treatment of the cells with N-acetyl-L-cysteine completely blocks the stimulated production of ceramides and DAG and totally inhibits the apoptosis of the pericytes induced by AGE-methylglyoxal.

We then defined an enzymatic target located upstream of the ceramides and DAG and which could also be found at the intersection of the two signalization pathways.

IV—Implication of Caspases: the Specific Proteases of Apoptosis

Recent studies revealed that a series of proteases from the ICE family (Interleukin-1 Converting Enzyme), renamed caspases (Cytosolic Aspartate-Specific Cysteine Proteases), played a key role in the transduction of apoptotic signals. Different classifications of these proteases were proposed on the basis of comparison criteria:

These enzymes were classified into two groups on the basis of the timing of their involvement in the apoptosis signalization pathway: the initiator caspases which are activated during the apoptosis initiation phase (caspases-2, -8, -10) and the effector caspases which can be activated in cascade by the initiator caspases, implicated in the apoptosis execution phase which is characterized by biochemical and morphological attacks on the cell (caspases-3, -6, -7, -9) (Nunez et al., 1998; Stennicke et al., 1998; Alnemri, 1999).

In contrast, the caspases could be classified differently into three subgroups on the basis of their substrate specificity: group I is constituted by caspases-1, -4, -5 (enzymes described as being implicated in inflammatory responses), group II is constituted by caspases-2, -3, -7, and group II is constituted by caspases-6, -8, -9, -10. Whereas the group II proteases require an aspartate residue in both the first and fourth positions of the proteolytic cleavage site (XDXXD), the group III proteases are more tolerant with regard to the fourth amino acid reside while exhibiting a preference for the aliphatic amino acids (XE[I/T/H/V]D) (Thornberry et al., 1997; Garcia-Calvo et al., 1998).

Finally, a phylogenetic analysis of the caspases allowed definition of three subfamilies: the ICE-like proteases (family of the caspases-1) grouping together caspases-1, -4, -5, -11; the IchII-like proteases (family of the caspases-2) grouping together the caspases-2, -9; and the CPP (cysteine protein protease) 32-like proteases (family of the caspases-3) grouping together the caspases-3, -6, -7, -8, -10 (Alnemri et al., 1996); Duan et al., 1996a, 1996b).

The caspases are inhibited in a specific manner in vitro and in vivo by synthetic peptides (most frequently, the tetrapeptides) made permeable to the cells by chemical groups blocking the terminal $NH_2$ and COOH functions and mimicking the cleavage site of their respective substrates.

We tested different synthetic inhibitor peptides to investigate whether the initiator and/or effector caspases were implicated in pericyte apoptosis induced by AGE-methylglyoxal. Three peptides described as specific inhibitors of a protease were tested:

the peptide z-VDVAD-fmk specific inhibitor of the initiator caspase-2, the peptide z-LETD-fmk specific inhibitor of caspase-8, and the peptide z-LEHD-fmk specific inhibitor of caspase-9.

We also analyzed the effects of other modified peptides not having specificity in relation to a caspase or having a moderate specificity dependent on the accessibility of the enzyme and the intracellular concentration of the inhibitor:

the inhibitor z-VAD-fmk which inhibits a broad spectrum of caspases, including both initiator and effector caspases (Garcia-Calvo et al., 1998);

the peptide z-DEVD-fmk which presents an inhibitory effect of the CPP32-like proteases, acting principally on the effector caspase-3 (Nicholson et al., 1995) and in a less specific manner on caspases-6, -7, -8, -10 (Fernandes-Alnemri et al., 1995); and the peptide z-AEVD-fmk which is an inhibitor of the initiator caspase-10 and in a less specific manner of caspases-8, -9.

Figure 16:
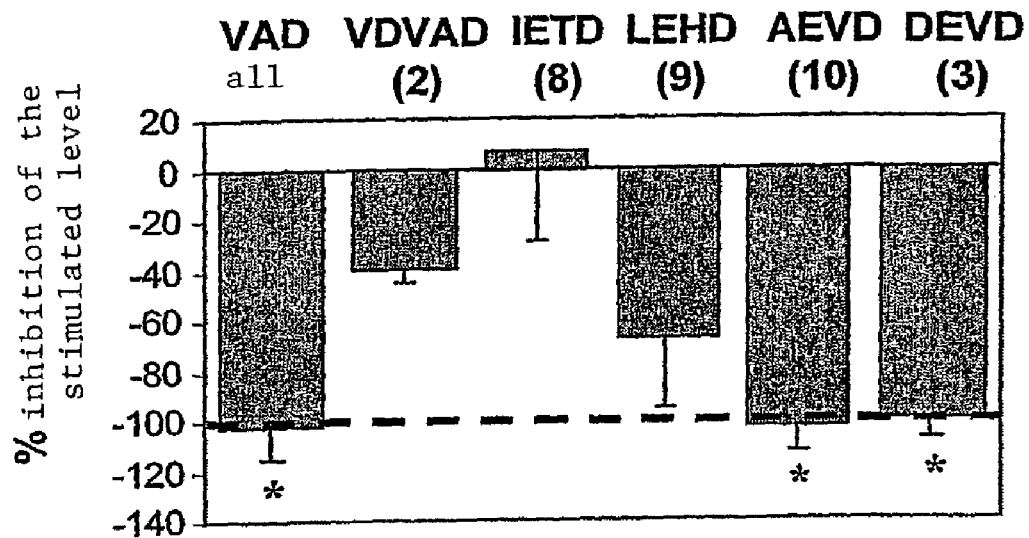
FIG. 16 shows the effect of caspase-inhibitor peptides on pericyte apoptosis induced by AGE-methylglyoxal.

2) Effect of the Caspase-Inhibitor Peptides on the Induced Apoptosis of Pericytes FIG. 16 shows the effect of caspase-inhibitor peptides on the apoptosis of pericytes induced by AGE-methylglyoxal. The cells were cultured during two passages (about 15 days) in the presence of AGE-methylglyoxal (or BSA control) and the inhibitory peptides z-VAD-fmk, z-DEVD-fmk, z-LETD-fmk, z-AEVD-fmk, z-VDVAD-fmk or z-LEHD-fmk (50 µM). Apoptosis was detected and quantitatively determined by annexin V labeling as described above. The results, expressed as % inhibition of the induced apoptosis, are the means of 6 independent experiments for z-VAD-fmk and z-DEVD-fmk, of 4 independent experiments for z-LEHD-fmk, and of 3 independent experiments for z-VDVAD-fmk, z-AEVD-fmk and Z-LETD-fmk.

The addition of 50 µM of z-VAD-fmk, z-DEVD-fmk, z-AEVD-fmk or z-LEHD-fmk to the culture medium resulted in an almost total inhibition of the apoptosis of the pericytes induced by AGE-methylglyoxal. On the other hand, the peptide z-LETD-fmk did not protect the cells against apoptosis and the peptide z-VDVAD-fmk induced a partial inhibition of the apoptosis induced by AGE-methylglyoxal (FIG. 16).

Figure 17:
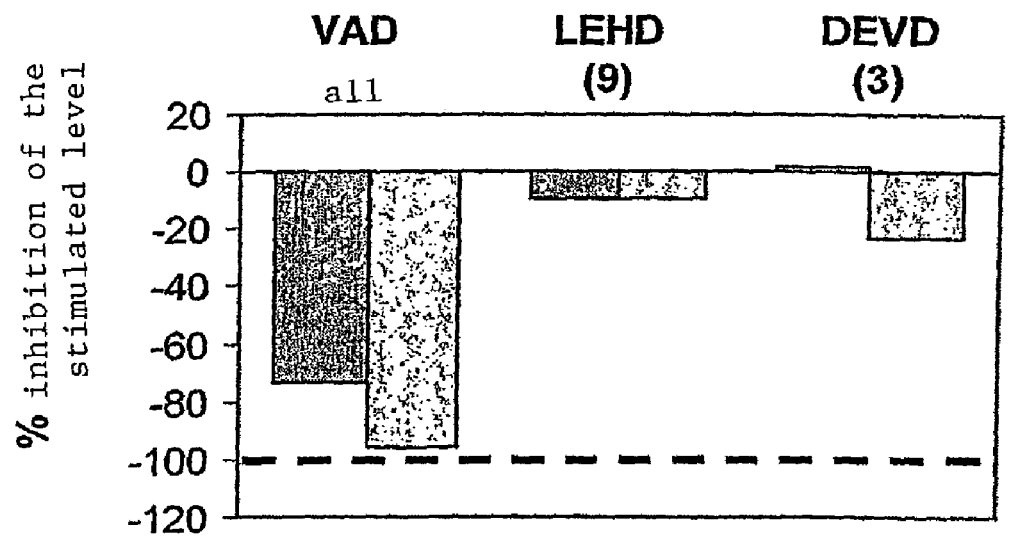
FIG. 17 shows the effect of the caspase-inhibitor peptides z-VAD-FMK, z-LEHD-fmk and z-DEVD-FMK (50 µM) on the stimulated production of ceramides and DAG in bovine retinal pericytes induced by AGE-methylglyoxal.

3) Effect of the Caspase-Inhibitor Peptides on the Stimulated Production of Ceramides and DAG in the Retinal Pericytes FIG. 17 shows the effects of the caspase-inhibitor peptides z-VAD-fmk and z-DEVD-fmk (50 µM) on the stimulated production of ceramides and DAG in bovine retinal pericytes induced by AGE-methylglyoxal. The ceramides and DAG were determined as described above. The results are expressed as % inhibition of the stimulated production and are the results of 2 independent experiments.

The effects of the inhibitory peptides on the production of ceramides and DAG differed: whereas the stimulated production of the two metabolic intermediaries was not affected in the pericytes treated with 50 µM of z-DEVD-fmk or z-LEHD-fmk, the peptide z-VAD-fmk blocked the overproduction of ceramides and DAG by 75% and 100% respectively.

4) Implication of Caspase-10 in the Apoptosis of Retinal Pericytes Induced by AGE a) Material The primary antibody directed against caspase-10, its respective blocking peptide, recombinant caspase-10 used as a positive control and the secondary anti-rabbit antibody were obtained from Biomol (France). The autoradiography films (Hyperfilm) and the ECL development reagents were purchased from Amersham (France). The SDS-page gels (ready gel Tris HCl 12%), the nitrocellulose membranes (porosity of 0.45 µM) for the immunoprints, the anti-goat secondary antibodies and the molecular weight markers (protein precision standards, broad range) were obtained from Bio-Rad (France).

The Mini-Protean II and Mini-Trans Blot systems from Bio-Rad were used for the electrophoresis and the electrotransfer.

b) Immunoblot

Preparation of the Samples

The pericytes (2 to 36-cm dishes), cultured for 15 days in the presence of 3 µM of AGE-methylglyoxal (or BSA control) as described in the application cited above, were deposited on an ice bed, washed 3 times with cold DPBS then scraped with a rubber policemen into 500 ml of cold recovery buffer (Tris-HCl 0.1 M pH 8 containing 4.4 µM of pepstatin A, 6 µM of leupeptin, 0.6 mM of PMSF and 10 mM of EDTA). The cell suspension was solubilized directly in the Petri dish by addition of 100 µl of Laëmmli 5× buffer (Tris-HCl 0.15 M pH 6.8 containing 5% of SDS, 12.5% of glycerol, 12.5% of β-mercaptoethanol and 1% of bromophenol blue) to limit the loss of cytoplasmic material. The DNA pellets, which made the solution viscous, were crushed mechanically using an intense piston in a syringe equipped with a 30 $G_{1/2}$ needle. The protein samples were then heated for 3 minutes at 100° C. prior to being deposited on polyacrylamide gel.

Polyacrylamide Gel Electrophoresis Under Denaturant Conditions (SDS-Page)

Electrophoresis was performed under reducing (β-mercaptoethanol) and denaturant (SDS) conditions using the Laëmmli technique (Laëmmli U.K., 1970).

Aliquots of pericyte lysates (20 µg) were deposited on a polyacrylamide gel (ready gel Tris-HCl from Bio-Rad) constituted of a 4% acrylamide concentration gel and a 12% acrylamide separation gel. Electrophoresis of the proteins was performed at 100 V (concentration gel) then 200 V (separation gel) in migration buffer (Tris 25 mM, glycine 0.19 M, SDS 0.1%) until the bromophenol blue (marking the migration front) reached the bottom of the gel. Molecular mass markers (250, 150, 100, 75, 50, 37, 25, 15, 10 kDa) were also deposited to calibrate the migration of the proteins.

The gel was then used for an electrotransfer of the proteins and then stained with Coomassie blue.

Electrotransfer of the Proteins Onto Nitrocellulose Membranes:

At the end of electrophoresis, the membrane, the sheets of Wattman paper and the foam sponges (Scotch Brite, 3M) were equilibrated for 10 minutes in cold transfer buffer (Tris 25 mM pH 8.3, glycine 192 mM, methanol 20% (v/v)). The sandwich was created by semi-immersion: the membrane and the gel were superposed and then encased on both sides by a paper and a sponge. The assembly placed in the tank was immersed in the transfer buffer and the proteins were transferred from the gel (cathode) to the nitrocellulose membrane (anode) electrophoretically at 100 V for 45 minutes at 4° C. and under magnetic agitation.

Immunodetection of the Transferred Proteins

The antigenic material used in our study was of bovine origin. Since we did not have available primary antibodies directed against bovine material, our choice was to use polyclonal antibodies having cross immunoreactivity with different species (humans, mouse and rat).

Buffers Employed:
TBS buffer (Tris Buffer Saline): Tris-HCl 10 mM pH 8.0, NaCl 150 mM
TTBS buffer: 0.05% of Tween 20 in TBS
Antibody dilution buffer: BSA 1% in TTBS
Membrane saturation buffer: milk 10% in TTBS
Visualization of the Proteins Antigenic Reaction After electrophoresis of the proteins and transfer, the nitrocellulose membrane was stained with ponceau red to mark the migration paths of the proteins and then decolored. The non-specific binding sites of the membrane were blocked by incubation in adequate saturation binder for 60 minutes at ambient temperature under gentle agitation (or alternatively overnight at 4° C.). The membrane was washed three times (15 minutes then 5 and 5 minutes) in TTBS buffer prior to being incubated for 2 hours with human anti-caspase-10 primary antibody (1/2000) diluted in the dilution buffer. A second series of washings in TTBS preceded the second incubation (1 hour 30 minutes) with anti-rabbit secondary antibody coupled to horseradish peroxidase (1/6000). The membrane was again washed in TTBS then rinsed for 5 minutes in TBS prior to being visualized with ECL.

ECL Development

The membrane was dried quickly on absorbent paper, incubated with the chemoluminescence detection solution from the ECL kit for 1 minute then enveloped in Saran film. It was then exposed to an autoradiographic film for a duration of 8 minutes and the films were developed.

c) Results

Figure 19:
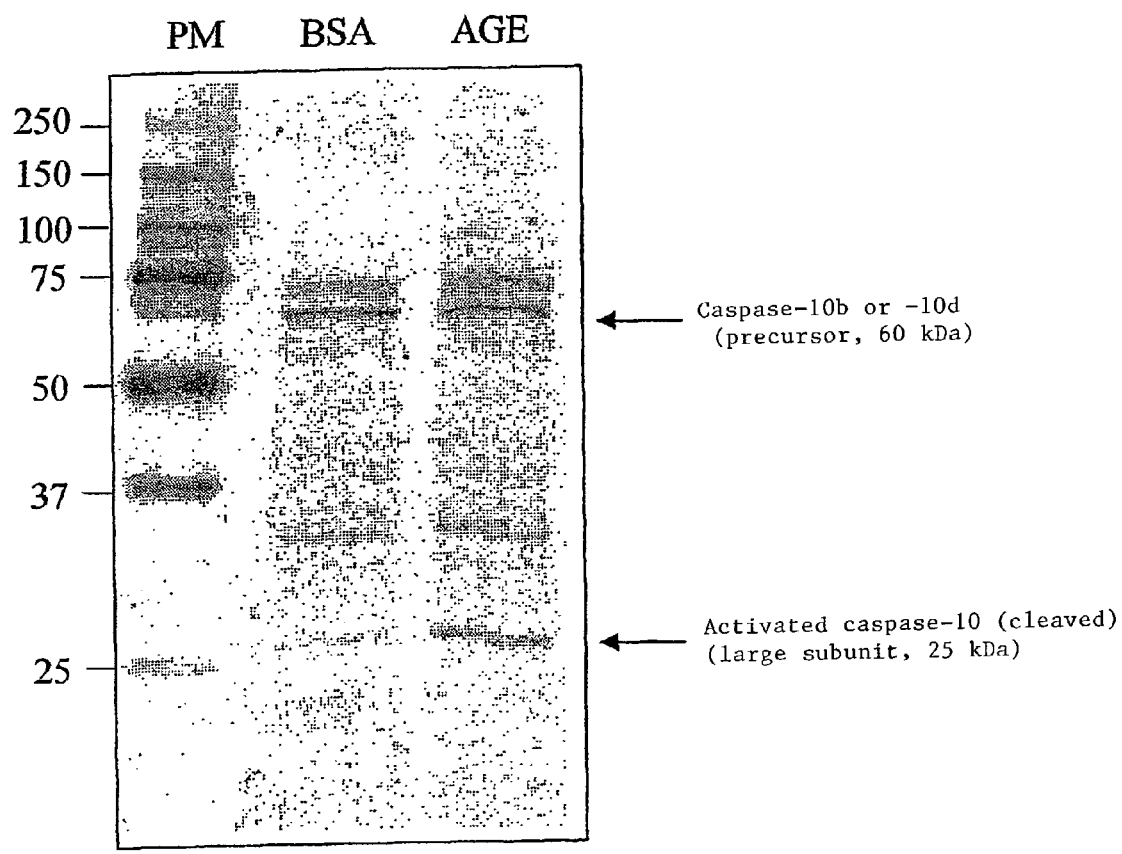
FIG. 19 is a Western blot with a human anti-caspase-10 antibody on pericyte cell lysates treated or not treated with AGE.

These results reinforce the previous results from the studies in which only caspase-inhibitor peptides were used. These results illustrated in FIG. 19 show by direct analysis with a specific antibody that the large subunit (25 kDa) of caspase-10 activated from its precursor (caspase-10b or -10d) is clearly present in the pericytes incubated with AGE suggesting that there is indeed activation of caspase-10 during the retinal pericyte apoptosis induced by AGE.

5) Conclusion

The protector effect of the peptide z-VAD-fmk (broad-spectrum caspase inhibitor) against pericyte apoptosis demonstrated the activation of caspases in the apoptotic signal transduction pathway. In the pericytes cultured with this inhibitor peptide, the production of ceramides and DAG induced by AGE-methylglyoxal was blocked, which thereby suggests the implication of an initiator caspase (caspases-2, -8, 10) controlling the production of ceramides and DAG.

In an initial step, we investigated whether the initiator caspase-8 was the enzyme activated in response to AGE-methylglyoxal. Incubation of the cells with their specific inhibitor z-LETD-fmk did not result in blocking the apoptosis. Caspase-8 thus does not appear to be implicated in the apoptosis of the pericytes.

We incubated the pericytes in the presence of the inhibitor peptide z-VDVAD-fmk, which is specific for this caspase, to determine whether the initiator caspase-2 participated in the transduction of the signal leading to apoptosis. The peptide z-VDVAD-fmk partially inhibited the apoptosis induced by AGE-methylglyoxal, suggesting that the initiator caspase-2 appears to be implicated in the apoptosis of the pericytes.

We also analyzed the effects of the peptide z-AEVD-fmk, described as an inhibitor of the initiator caspase-10 and a less specific inhibitor of the initiator caspase-8 and the effector caspase 9. The protector effect of this peptide against pericyte apoptosis suggests activation of caspase-10 and/or caspase-9. The involvement of caspase-8 was excluded by the absence of an effect of z-LETD-fmk on apoptosis. The peptide z-LEHD-fmk, an inhibitor described as specific for the effector caspase-9, also had a protector effect against apoptosis of the pericytes but without affecting the overproduction of DAG or ceramides induced by AGE-methylglyoxal. This result suggests that caspase-9, blocked by z-LEHD-fmk, intervenes downstream of the production of DAG and ceramides. Thus, caspases-2, -9 and -10 appear to participate in the transduction of the apoptotic signal in retinal pericytes.

The protector effect of the peptide z-DEVD-fmk against apoptosis of the pericytes suggests that the two proposed metabolic pathways converge at the same caspase from the family of the CPP32-like proteases. Treatment of pericytes with this inhibitor peptide did not affect the overproduction of ceramides and DAG induced by AGE-methylglyoxal. This results thus allows us to conclude that the caspase(s) blocked by z-DEVD-fmk intervene(s) downstream from the ceramides and DAG. Moreover, inhibition of apoptosis observed in the presence of z-DEVD-fmk does not appear to be linked to inhibition of the initiator caspases-2, -8, -10 because the production level of the ceramides and DAG was not affected. Similarly, inhibition of apoptosis by z-LEHD-fmk, specific for caspase-9, does not appear to be linked to the inhibition of the initiator caspases because the level of DAG and ceramides was not affected. We can, therefore, conclude that the two metabolic pathways converge at two effector caspases, caspase-9 and caspase-3, and perhaps caspase-6 and caspase-7 of the CPP32-like proteases, intervening in the apoptosis execution phase.

Figure 18:
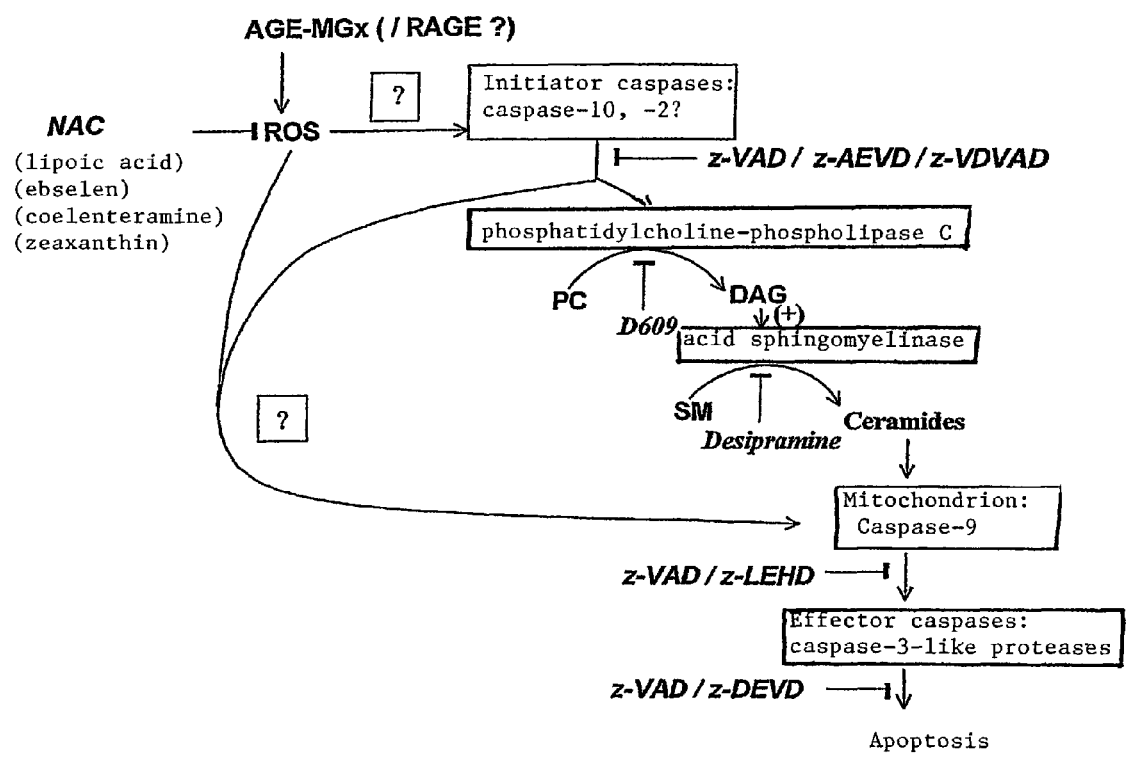
FIG. 18 represents the signalization pathway leading to pericyte apoptosis envisaged on the basis of the invention.

FIG. 18 shows a signalization pathway leading to apoptosis of the pericytes. AGE-methylglyoxal induces an oxidant stress which appears to activate an initiator caspase (caspase-2 or -10). Activation of this caspase activates an enzymatic cascade implicating in a first stage a phosphatidyl-choline-phospholipase C, then an acid sphingomyelinase and then caspase-9 and an effector caspase from the CPP32-like proteases. We were able to determine that these caspases-9 and -3 are located at the intersection of two metabolic pathways. In contrast, we were unable to determine whether the two pathways diverge downstream from the initiator caspase or whether the oxidant stress remains at the intersection of the two pathways.

The described studies performed in the framework of the invention clearly demonstrate that an initiator caspase, probably caspase-10, is implicated in the cascade of biochemical events leading to the apoptosis of the pericytes induced by the AGE. This involvement is supported by experimental arguments based on a purely pharmacological approach using specific peptide inhibitors of different caspases. FIG. 19 shows that caspase-10 is clearly activated when the bovine retinal pericytes are subjected to AGE. In fact, by immuno-detection on nitrocellulose using a specific antibody that recognized the cleaved and active form (large subunit, 25 kDa) of caspase-10 from its precursor (caspase-10b (FADD-like interleukin-1-converting enzyme-2, FLICE-2) or caspase-10d, 60 kDa), it was possible to detect the large caspase subunit (25 kDa) activated in the cells treated by AGE whereas it was almost inexistent in the case of the cells treated with the BSA control (see FIG. 19) although the amount of precursor (caspase-10b or -10d) was similar under the two conditions (see FIG. 1).

The subject matter of the following Bibliographic References is incorporated herein by reference.

1) Aiello L P, Gardner T W, King G L, Blankenship G, Cavallerano J D, Ferris F L and Klein R (1998). Diabetic retinopathy. *Diabetes care* 21:277-293
2) Algvere P V, Gouras P and Dafgard Kopp E (1999). Long-term outcome of RPE allografts in nonimmunosuppressed patients with AMD. *Eur J. Ophthalmol.* 9: 217-230
3) Alnemri E S (1999). Hidden powers of the mitochondria. *Nature Cell. Biology* 1: 40-42
4) Alnemri E S, Livingston D J, Nicholson D W, Salvesen G, Thornberry N A, Wong W W and Yuan J (1996). Human ICE/CED-3 Protease Nomenclature. *Cell* 87: 171
5) Andrieu N, Salvayre R and Levade T (1994). Evidence Against Involvement of the acid lysosomal Sphingomyelinase in the TNF and Interleukin-1-induced Sphingomyelin Cycle and Cell Proliferation in Human Fibroblasts. *Biochem J* 303: 341-345
6) Ansari N H, Zhang W, Fulep E and Mansour A (1998). Prevention of pericyte loss by trolox in diabetic rat retina. *J Toxicol. Environm. Health* 54: 467-478
7) Beisswenger P J, Makita Z, Curphey T J, Moore L L, Smith J, Brinck-Johnsen T, Bucala R and Vlassara H (1995). Formation of Immunochemical Advanced Glycosylation End Products Precedes and Correlate with Early Mannifestations of Renal and Retinal Diseases in Diabetes. *Diabetes* 44: 824-829

8) Bierhaus A, Chevion S, Chevion M, Hofmann M, Quehenberger P, Illmer T, Luther T; Berentshtein E, Tritschler H, Muller M, Wahl P, Ziegler R and Naworth P (1997). Advanced glycation end product-induced activation of NF-KB is suppressed by α-lipoic acid in cultured endothelial cells. *Diabetes* 46: 1481-1490

9) Bligh E G and Dyer W J (1959). A rapid method of total lipid extraction and purification. *Can J. Biochem. Physiol.* 37: 911-917

10) Brett J, Schmidt A M, Yan S D, Zou Y S, Weidman E, Pinsky D, Nowygrod R, Neeper M, Przysiecki C, Shaw A, Mighelli A and Stern D (1993). Survey of the distribution of a newly characterized receptor for advanced glycation end products in tissues. *Am. J. Pathol.* 143: 1699-1712

11) Chibber R, Molinati P A, Rosatto N, Lamboume B and Kohner E M (1997). Toxic action of Advanced Glycation End Products on Cultured Retinal Capillary Pericytes and Endothelial Cells: Relevance to Diabetic Retinopathy. *Diabetologia* 40: 156-164

12) Cogan D G, Toussaint D and Kuwabara T (1961). Retinal vascular patterns IV. Diabetic retinopathy. *Arch. Ophthalmol.* 60: 100-112

13) DCCT—The Diabetes Control Complications Trial Research Group. The effects of intensive treatment of diabetes on the development and progression of long-term complications in insulin-dependent diabetes mellitus. *N. Engl J Med* 1993, vol 239, p 977-986

14) Degenhardt T P, Thorpe S R and Baynes J W (1998). Chemical modification of Proteins by Methylglyoxal. *Cell. Mol. Biol.* 44: 1139-1145

15) Desai S D and Blanchard J (1998). In vitro evaluation of pluronicF127-based controlled-release ocular delivery systems for pilocarpine. *J Pharm. Sci.* 87-226-230

16) Duan H, Chinnaiyan A M, Hudson P L, Wing J P, He W W and Dixit V M (1996a). ICE-LAP3, a novel Mammalian Homologue of *Caenorhabditis elegans* Cell Death Protein Ced3 is Activated During Fas- and TNF-induced Apoptosis. *J Biol. Chem.* 271: 1621-1624

17) Duan H, Orth K, Chinnaiyan A M, Poirier G G, Froelich C J, He W W and Dixit W M (1996.b). ICE-LAP6, a Novel Member of the ICE/Ced-3 Gene Family, is Activated by Cytotoxic T Cell Protease Gramzyme B. *J Biol. Chem.* 271: 16720-16724

18) Early Treatment Diabetic Retinopathy Study Research group: grading diabetic retinopathy from stereoscopic color fundus photographs: an extension of the modified Airlie House classification: ETDRS Report No. 10, 1991. *Ophthalmology*, vol 98, p786-791

19) Femandes-Alnemri T, Armstrong R T, Krebs J, Srinivasula S M, Wang L, Bullrich F, Fritz L C, Trapani J A, Tomaselli K J, Litwack G and Alnemri E S (1995). In vitro Activation of CPP32 and Mch3 by Mch4, a Novel Apoptotic Cysteine Protease Containing Two FADD-like Domains. *Proc. Acad. Natl. Sci. USA* 93: 7464-7469

20) Frank RN. Diabetic retinopathy. Chapter 1 in Progress in Retinal and Eye Research Vol 14 No. 2 Elsevier Science Ltd (Great Britain), 1995, p 361-392

21) Freedman K A, Klein J W and Crosson C E (1993). Beta-cyclodextrins enhance bioavailability of pilocarpine. *Curr. Eye Res.* 12: 641-647

22) Friedenwald J S (1950). Diabetic retinopathy *Am. J. Ophthalmol.* 33: 1187-1199

23) Friederich R L (1974). The pilocarpine Ocusert: a new drug delivery system. *Ann. Ophthalmol.* 6: 1279-1284

24) Garcia-Calvo M, Peterson E P, Leiting B, Ruel R, Nicholson D W and Thornberry N A (1998). Inhibition of Human Caspases by Peptide-based and Macromolecular Inhibitors. *J Biol. Chem.* 273: 32608-32613

25) Genestier L, Prigent A-F, Paillot R, Quemeneur L, Durand I, Banchereau J, Revillard J P and Bonnefoy-Bérard N (1998). Caspase-dependant ceramide Production in FAS- and HLA Class I-mediated Peripheral T Cell Apoptosis. *J. Biol. Chem.* 273: 5060-5066

26) Gluzman Y, Reichl H and Solnick D (1982) in Eukaryotic Viral Vectors (Gluzman Y, ed) pp 187-192, ColdSpring Harbor Laboratory, Cold Spring Harbor, N.Y.

27) Graham F L, Smiley J, Russel W C and Nairn R (1977). Characteristics of a human cell line transformed by DNA from human adenovirus type 5. *J Gen. Virol.* 36: 59-74

28) Grange J D (1995). Diabetic Retinopathy. Paris, Milan, Barcelona: Masson: 632

29) Hammes H P, Martin S, Federlin K, Geisen K and Brownlee M (1991). Aminoguanidine Treatment inhibits the Development of Experimental Diabetic Retinopathy. *Proc. Natl Acad. Sci. USA* 88:11555-11558

30) Hangai M, Tanihara H, Honda Y and Kaneda Y (1998) In Vivo delivery of phosphorothioate oligonucleotides into the murine retina. *Arch. Ophthalmol.* 116: 342-348

31) Jaffrezou J P, Chen G, Duran G E, Muller C, Bordier C, Laurent G, Sikic B I and Levade T (1995). Inhibition of lysosomal acid sphingomyelinase by agents which reverse multidrug resistance. *Biochem. Biophys. Acta.* 1266:1-8

32) Kahn H A et Hiller R (1974). Blindness caused by diabetic retinopathy. *Am. J Ophthalmol.* 78: 58-67

33) Karesh J W (1987). Polytetrafluoroethylene as a graft material in ophthalmic plastic and reconstructive surgery. An experimental and clinical study. *Ophthal. Plast. Reconstr. Surg.* 3: 179-185

34) Kuwabara T and Cogan D G (1963). Retinal vascular patterns VI. Mural cells of the retinal capillaries. *Archs. Ophthal.* 69: 492-502

35) Lai C M, Shen W Y, Constable I and Rakoczy P E (2000). The use of adenovirus-mediated gene transfer to develop a rat model for photoreceptor degeneration. *Invest. Ophthalmol. Vis. Sci.* 41: 580-584

36) Lander H M, Tauras J M, Ogiste J S, Hori O, Moss R A and Schmidt A M (1997). Activation of the receptor for advanced glycation end products triggers a p21 rasdependent mitogen-activated protein kinase pathway regulated by oxidant stress. *J. Biol. Chem.* 272: 17810-17814

37) Leahey A B, Gottsch J D and Syark W J (1993). Clinical experience with N-butyl cyanoacrylate. (Nexacryl) tissue adhesive. *Ophthalmol.* 100: 173-180

38) Lecomte M, Paget C, Ruggiero D, Wiernsperger N and Lagarde M (1996). Docosahexaenoic acid is a major n-3 polyunsaturated fatty acid in bovine retinal microvessels. *J Neurochem.* 66: 2160-2167

39) Leeds J M, Henry S P, Bistner S, Scherill S, Williams K and Levin A A (1998). Pharmacokinetics of an antisense oligonucleotide injected intravitreally in monkeys. *Drug Metab. Dispos.* 26: 670-675

40) Li W, Liu X, Yanoff M, Cohen S and Ye X (1996). Cultured Retinal Capillary Pericytes Die by Apoptosis After an Abrupt Fluctuation from High to Low Glucose Levels: a Comparative Study With Retinal Capillary Endothelial Cells. *Diabetologia* 39: 537-547

41) Li W, Liu X, He Z, Yanoff M, Jian B and Ye X (1998). Expression of Regulatory genes by Retinal Pericytes After Rapid Glucose Reduction. *Invest. Ophthalmol. Vis. Sci.* 39: 1535-1543

42) Li W, Yanoff M, Jian B and He Z (1999) Altered mRNA levels of antioxidant enzymes in pre-apoptotic pericytes from human diabetic retinas. Cell. Mol. Biol. (Noisy-le-grand) 45: 59-66

43) Li W, Shen S, Khatami M and Rockey J H (1984). Stimulation of retinal capillary pericyte protein and collagen synthesis in culture by high glucose concentration. *Diabetes* 33: 785-789

44) Li W, Yanoff M, Liu X and Ye X (1997). Retinal Capillary Pericytes Apoptosis in Early Diabetic Retinopathy. *Chin. Med. J (Engl)* 110: 659-663

45) Lo TWC, Westwodd M E, McLellan A C, Selwoll T and Thornalley P J (1994). Binding and modification of proteins by methylglyoxal under physiological conditions. A kinetic and mechanistic study with Nα-acetylarginine, Nα-acetylcysteine, Nα-acetyllysine, and bovine serum albumin. *J. Biol. Chem.* 269: p32299-32305

46) Maillard L C (1912). Action of the amino acids on sugars: formation of melanoidines by methodic pathway. C R Hebd Sci, Acad Sci Paris, Vol 154, p 66-68)

47) Mandarino L J, Sundarraj N, Finlayson J and Hassel J R (1993). Regulation of fibronectin and laminin synthesis by retinal capillary endothelial cells and pericytes in vitro. *Exp. Eye Res.* 57: 609-621

48) Mathias S, Pena L A and Kolesnick R N (1998). Signal transduction of stress via ceramides. *Biochem. J* 335: 465-480

49) McLellan A C, Thornalley P J, Benn J and Sonksen P H (1994). Glyoxalase System in Clinical Diabetes Mellitus and Correlation with Diabetic Complications. *Clin. Sci.* 7: 21-29

50) Mizutani M, Kern T S and Lorenzy M (1996) Accelerated Death of Retinal Microvascular Cells in Human and Experimental Diabetic Retinopathy. *J Clin. Invest.* 97: 2883-2890

51) Müller-Decker K, Doppler C, Amtmann E and Sauer G (1988). Interruption of Growth Signal Transduction by an Antiviral and Antitumoral Xanthate compound. *Exp. Cell. Res.* 177: 295-302

52) Müller-Decker K (1989). Interruption of TPA-induced Signals by an Antiviral and Antitumoral Xanthate Compound: Inhibition of a Phospholipase C-type Reaction. *Biochem. Biophys. Res. Com.* 162: 198-205

53) Nathan D M, Fogel H A, Godine J E et al. (1991). Role of diabetologist in evaluating diabetic retinopathy. *Diabetes Care* 14: 26-33

54) Neeper M, Schmidt A M, Brett J, Yan S D, Wang F, Pan Y C, Elliston K, Stern D and Shaw A (1992). Cloning and expression of a cell surface receptor for advanced glycosylation end products of proteins. *J. Biol. Chem.* 267: 14498-15004

55) Nicholson D W, Ali A, Thornberry N A, Vaillancourt J P, Dink C K, Gallant M, Gareau Y, Griffin P R, Labelle M, Lazebnick Y A, Monday N A, Raju S M, Smulson N E, Yamin T T, Yu V L and Müller-Decker K (1995). Identification and Inhibition of the ICE/CED-3 Protease Necessary for Mammalian Apoptosis. Nature 376: 37-43

56) Nishikawa T, Edelstein D, Hu X L, Yamagishi S I, Matsumura T, Kaneda Y, Yorak M A, Beebe D, Dates P J, Hammes P J, Giardino I and Brownlee M (2000). Normalizing mitochondrial superoxide production blocks three pathways of hyperglycaemic damage. *Nature* 404: 787-790

57) Nunez G, Benedict M A, Hu Y and Inohara N (1998). Caspases: the proteases of the apoptotic pathway. *Oncogene* 17: 3237-3245

58) Nuyts R M, Kooijman-DeGroot M J, Prins and Pels E (1999). Use of a polyurethane patch for temporary closure of a sterile corneal perforation. *Arch. Ophthalmol.* 117: 1427-1429

59) Oganesian A, Gabrielian K, Ernest J T and Patel S C (1999). A new model of retinal pigment epithelium transplantation with microspheres. *Arch. Ophthalmol.* 117: 1192-1200

60) Okasaki T, Kondo T, Kitano T and Tashima M (1998). Diversity and Complexity of Ceramides Signaling in Apoptosis. *Cell. Signal.* 10: 685-692

61) Paget C, Lecomte M, Ruggiero D, Wiernsperger N and Lagarde M (1998). Modification of Enzymatic Antioxidants in Retinal Microvascular by glucose or Advanced Glycation End Products. *Free. Radic. Biol. Med.* 25: 121-129

62) Palmberg P F (1977). Diabetic retinopathy. *Diabetes* 26: 703-709

63) Podesta F, Romeo G, Liu W H, Krajewski S, Reed J C, Gerhardinger C and Lorenzy M (2000). Bax is Increased in the Retina of Diabetic Subjects and in Associated With Pericytes Apoptosis In Vivo and In Vitro. *Am. J Pathol.* 156: 1025-1032

64) Porta M, Molinatti P A, Dosso A A, Williams F M K, Brooks R A and Kohner E M (1994). Growth of bovine retinal pericytes and endothelial cells in high glucose concentrations. *Diabetes and Metabolism* 20: 25-30

65) Preiss J, Loomis C R, Bishop W R, Stein R, Niedel J E and Bell R M (1986). Quantitative measurement of sn-1,2-diacylglycerols present in platelets, hepatocytes, and ras- and sis-transformed normal kidney cells. *J. Biol. Chem.* 261: 8597-8600

66) Rubin A L, Stenzel K H, Miyata T, White M J and Dunn M (1973). Collagen as a vehicle for drug delivery. Preliminary report *J. Clin. Pharmacol.* 13: 309-312

67) Ruggiero-Lopez D, Rellier N, Lecomte M, Lagarde M and Wiemsperger N (1997). Growth Modulation of Retinal Microvascular Cells by Early and Advanced Glycation Products. *Diabetes Res. Clin. Pract.* 34: 135-142

68) Schaffner W and Weissmann C (1973). A rapid, sensitive and specific method for the determination of protein in dilute solution. *Anal. Biochem.* 50: 502-504

69) Schalkwijck C G, Ligtvoet N, Twaalfhoven H, Jager A, Blaauwgeers H G T, Schlingemann R O, Tarnow L, Parving H H, Stehouwer C D A and van Hinsbergh V W M (1999). Amadori Albumin in Type I diabetic patients. Correlation with markers of endothelial function, association with diabetic nephropathy, and localization in retinal capillaries. *Diabetes* 48: 2446-2453

70) Schmidt A M, Vianna M, Gerlach M, Brett J, Ryan J, Kao J, Esposito C, Hegarty H, Hurley W, Clauss M, Wang F, Pan Y CE, Tsang T C and Stern D (1992). Isolation and characterization of two binding proteins for advanced glycosylation end products from bovine lung which are present on the endothelial cell srf ace. *J Biol. Chem.* 267: 14987-14997

71) Schuchman E H, Suchi M, Takahashi T, Sandhoff K and Desnick R J (1991). Human acid sphingomyelinase. Isolation, nucleotide sequence and expression of the full-length and alternatively spliced cDNAs. *J Biol. Chem.* 266: 8531-8539

72) Schütze S, Potthoff K, Machleidt T, Berkovic D, Wiegmann K and Krönke M (1992). TNF Activates NF-kB by Phosphatidylcholine-specific Phospholipase C-Induced "Acidic" Sphingomyelin Breakdown. *Cell.* 71: 765-776

73) Shinohara M, Thornalley P J, Giardino I, Beisswenger P, Thorpe S R, Onorato J and Brownlee M (1998). Overexpression of glyoxalase-I in bovine endothelial cells inhibits intracellular advanced glycation endproduct formation and prevents hyperglycemia-induced increases in macromolecular endocytosis. *J. Clin. Invest.* 101: 1142-1147
74) Soulis T, Thallas V, Youssef S, Gilbert R E, McWilliam B G, Murray-Mcltosh R P and Cooper M E (1997). Advanced glycation end products and their receptors co-localise in rat organs susceptible to diabetic microvascular injury. *Diabetologia* 40: 619-628
75) Stennicke H R and Salvesen G S (1998) Properties of the caspases. *Biochem. Biophys. Acta.* 1387: 17-31
76) Stitt A W, Li Y M, Gardiner T A, Bucala R, Archer D B and Vlassara H (1997). Advanced Glycation End Products (AGES) Co-localize With AGE Receptors in the Retinal Vasculature of Diabetic and AGE-infused Rats. *Am. J. Pathol.* 150: 523-535
77) Su T and Gillies M C (1992). A simple method for the in vitro culture of human retinal capillary endothelial cells. *Invest. Ophthalmol. Vis. Sci.* 33: 2809-2813
78) Thornalley P J (1998). Cell activation by glycated proteins. AGE receptors, receptor recognition factors and functional classifications of AGEs. *Cell Mol. Biol.* (*Noisy-le-qrand*) 44: 1013-1023
79) Thornalley P J (1999). The clinical significance of glycation. *Clin. Lab.* 45: 261-273
80) Thornberry N A, Rano T A, Peterson E R, Rasper D M, Timkey T, Garcia-Calvo M, Houtzager V M, Nordstrom P A, Roy S, Vaillancourt J P, Chapman K T and Nicholson D W (1997). A combinatorial Approach Defines Specificities of Members of the Caspase Family and Granzymes B. *J Biol. Chem.* 272: 17907-17911
81) UKPDS(a)—UK Prospective Diabetes Study Group. Intensive blood-glucose control with sulphonylureas or insulin compared with conventional treatment and-risk of complications in patients with type 2 diabetes (UKPDS 33) *Lancet* 1998, vol 352 (9131), p 837-853
82) UKPDS(b)—UK Prospective Diabetes Study Group. Effect of intensive blood-glucose control with metformin on complications in overweight patients with type 2 diabetes (UKPDS 34) *Lancet* 1998, vol 352 (9131), p 854-865
83) Vandervoort J and Ludwig A (999). Evaluation of pilocarpine loaded gelatin particles for topical ophthalmic use. *J. Pharm. Belg.* 54: 85-86
84) Vlassara H, Li Y-M, Imani F, Wojciechowicz D, Yang Z, Liu FT and Cerami A (1995). Identification of galectin-3 as a high-affinity binding protein for advanced glycation end products (AGE): a new member of the AGE receptor complex. *Mol. Med.* 1: 634-646
85) Wang E, Norred W P, Bacon C W, Riley R T and Mirrill A H Jr (1991). Inhibition of Sphingolipid Biosynthesis by Fumonisins. Implication for Diseases Associated with Fusarium Monliforme. *J. Biol. Chem.* 266: 14486-14490
86) Westwood M E and Thornalley P J (1995) Molecular characteristics of methylglyoxal-modified bovine and human serum albumins. Comparison with glucose-derived advanced glycation endproducts-modified serum albumins. *J. Protein Chem.* 14: 359-372
87) Wilkins M R, Occleston N L, Kotecha A, Waters L and Khaw P T (2000). Sponge delivery variables and tissues levels of 5-fluorouracil. Br. *J. Ophthalmol.* 84: 92-97
88) Yamagishi S, Hsu C C, Taniguchi M, Harada S, Yamamoto Y, Ohsawa K, Kobayashi K and Yamamoto H (1995). Receptor mediated Toxicity to Pericytes of Advanced Glycosylation End Products: a Possible Mechanism of Pericyte Loss in Diabetic Microangiopathy. *Biochem. Biophys. Res. Commun.* 213: 681-687
89) Yan S D, Schmidt A M, Anderson G M, Zhang J, Brett J, Zou Y S, Pinsky D and 0 Stern D (1994). Enhanced cellular oxidant stress by the interaction of advanced glycation end products with their receptors/.binding proteins. *J Biol. Chem.* 269: 9889-9897
90) Yang B Z, Makita Z, Horii Y, Brunelle S, Cerami A, Sehajpal P, Suthanthiran M and Vlassara H (1991). Two novel rat liver membrane proteins that bind advanced glycosylation end products: relationship to macrophage receptor for glucose-modified proteins. *J Exp. Med.* 174: 515-524
91) Zhu G, Mallery S R and Schwendeman S P (2000). Stabilization of proteins encapsulated in injectable poly (lactide-co-glycolide). *Nature Biotechnol.* 18: 52-57
92) Zuckert W R, Marquis H and Goldfine H (1998). Modulation of enzymatic activity and biological function of *Listeria monocytogenes* broad-range phospholipase C by amino acid substitution and by replacement with the *Bacillus cereus* ortholog. *Infect. Immun.* 66: 4823-4831
93) Zurowska-Pryczkowska X, Sznitowska M and Janicki S (1999). Studies on the effect of pilocarpine incorporation into a submicron emulsion on the stability of the drug and the vehicle. *Eur. J Pharm. Biopharm.* 47: 255-260

What is claimed is:

1. A method of treating diabetic retinopathy comprising administering to a mammal a therapeutically effective amount of a caspase inhibitor of retinal pericyte apoptosis, wherein the caspase inhibitor is a peptide modified chemically by a benzyloxycarbonyl group (z) of the N-terminal end or by an (O-methyl)-fluoromethyl ketone group (fmk) of the C-terminal end.

2. A method of treating diabetic retinopathy comprising administering to a mammal a therapeutically effective amount of a caspase inhibitor of retinal pericyte apoptosis, wherein the caspase inhibitor is tripeptide z-VAD-fmk.

3. A method of treating diabetic retinopathy comprising administering to a mammal a therapeutically effective amount of a caspase inhibitor of retinal pericyte apoptosis, wherein the caspase inhibitor is an inhibitor of the initiator caspase-10 and is peptide z-AEVD-fmk.

4. A method of treating diabetic retinopathy comprising administering to a mammal a therapeutically effective amount of a caspase inhibitor of retinal pericyte apoptosis, wherein the caspase inhibitor is an inhibitor of the initiator caspase-2 and is peptide z-VDVAD-fmk.

5. A method of treating diabetic retinopathy comprising administering to a mammal is therapeutically effective amount of a caspase inhibitor of retinal pericyte apoptosis, wherein the caspase inhibitor is an inhibitor of the effector caspase-3 and is peptide z-DEVD-fmk.

* * * * *